United States Patent
Kaneko et al.

(10) Patent No.: US 9,597,283 B2
(45) Date of Patent: Mar. 21, 2017

(54) INJECTABLE DEPOT FORMULATION COMPRISING OPTICALLY ACTIVE TOLVAPTAN AND PROCESS OF PRODUCING THE SAME

(71) Applicant: OTSUKA PHARMACEUTICAL CO., LTD., Tokyo (JP)

(72) Inventors: Daiki Kaneko, Osaka (JP); Takakuni Matsuda, Osaka (JP); Kenichi Miyata, Osaka (JP); Kai Suzuki, Osaka (JP); Hiroyuki Fujiki, Osaka (JP); Shizuo Kinoshita, Osaka (JP); Koji Ohmoto, Osaka (JP); Miki Aihara, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/758,108

(22) PCT Filed: Dec. 27, 2013

(86) PCT No.: PCT/JP2013/085355
§ 371 (c)(1),
(2) Date: Jun. 26, 2015

(87) PCT Pub. No.: WO2014/104412
PCT Pub. Date: Jul. 3, 2014

(65) Prior Publication Data
US 2015/0352041 A1 Dec. 10, 2015

Related U.S. Application Data

(60) Provisional application No. 61/747,005, filed on Dec. 28, 2012.

(51) Int. Cl.
*A61K 9/16* (2006.01)
*A61K 9/00* (2006.01)
(Continued)

(52) U.S. Cl.
CPC .......... *A61K 9/0019* (2013.01); *A61K 9/0024* (2013.01); *A61K 9/10* (2013.01);
(Continued)

(58) Field of Classification Search
CPC .... A61K 9/1647; B81Y 30/00; C01P 2004/61
See application file for complete search history.

(56) References Cited

U.S. PATENT DOCUMENTS 5,258,510 A 11/1993 Ogawa et al.
5,559,230 A 9/1996 Ogawa et al.
(Continued)

FOREIGN PATENT DOCUMENTS

JP 04-154765 5/1992
JP 4210355 1/2009
(Continued)

OTHER PUBLICATIONS

Jun Matsubara et al., "An Efficient Synthesis of Optical Isomers of Vasopressin $V_2$ Receptor Antagonist OPC-41061 by Lipase-Catalyzed Enantioselective Transesterification", Heterocycles, vol. 54, No. 1, 2001, pp. 131-138 (2001).

(Continued)

*Primary Examiner* — Carlos Azpuru
(74) *Attorney, Agent, or Firm* — Finnegan, Henderson, Farabow, Garrett & Dunner, L.L.P.

(57) ABSTRACT

This invention provides an injectable formulation to be administered intramuscularly or subcutaneously that is used for the prevention or treatment of polycystic kidney disease, and that can maintain a therapeutically effective blood concentration of tolvaptan for a long period of time; and a process for producing the same. More specifically, this invention relates to an injectable depot formulation comprising (1) a particle containing optically active tolvaptan as (Continued)

an active ingredient and (2) a pharmaceutically acceptable carrier for injection, and a process for producing the same.

14 Claims, 6 Drawing Sheets

(51) Int. Cl.
    *A61K 47/38*     (2006.01)
    *A61K 47/32*     (2006.01)
    *A61K 47/10*     (2017.01)
    *A61K 9/10*     (2006.01)
    *A61K 9/14*     (2006.01)
    *A61K 31/55*     (2006.01)

(52) U.S. Cl.
    CPC ............... *A61K 9/14* (2013.01); *A61K 9/1635* (2013.01); *A61K 9/1647* (2013.01); *A61K 9/1652* (2013.01); *A61K 9/1688* (2013.01); *A61K 9/1694* (2013.01); *A61K 31/55* (2013.01); *A61K 47/10* (2013.01); *A61K 47/32* (2013.01); *A61K 47/38* (2013.01)

(56) References Cited

U.S. PATENT DOCUMENTS 5,753,677 A     5/1998     Ogawa et al.
5,985,869 A     11/1999     Ogawa et al.

FOREIGN PATENT DOCUMENTS

WO     WO 2009/001968     12/2008
WO     WO 2013/180310     12/2013

OTHER PUBLICATIONS

Hiroshi Yamashita, et al., "Practical Synthesis of Both Enantiomers of Vasopressin $V_2$ Receptor Antagonist OPC-47061 Using The Catalytic Asymmetric Hydrogenation", Heterocycles, vol. 56, 2002, pp. 123-128 (2002).
Lu Yin, et al., "Efficient and promising asymmetric preparation of enantiopure tolvaptan via transer hydrogenation with robust catalyst", Tetrahedron: Asymmetry, vol. 21, pp. 2390-2393 (2010).
International Search Report issued by the European Patent Office in International Application No. PCT/JP2013/085355, mailed Apr. 2, 2014 (2 pages).
Written Opinion of the International Searching Authority issued by the European Patent Office in International Application No. PCT/JP2013/085355, mailed Apr. 2, 2014.

(1)

(2)

S-tolvaptan was subcutaneously injected twice, i.e., at 6 weeks of age and 10 weeks of age. Each value indicates the mean value ± SEM. (n=3-10)

R-tolvaptan was intramuscularly injected three times, i.e., at 14 weeks of age, 15 weeks of age, and 20 weeks of age. Each value indicates the mean value ± SEM. (n=9)

INJECTABLE DEPOT FORMULATION COMPRISING OPTICALLY ACTIVE TOLVAPTAN AND PROCESS OF PRODUCING THE SAME

TECHNICAL FIELD

The present invention relates to an injectable depot formulation that comprises a particle containing optically active tolvaptan and that is suitable as a depot injection to be administered intramuscularly or subcutaneously, and a process for producing the same.

BACKGROUND ART

Patent Literature 1 discloses tolvaptan represented by Formula (I), which is useful as a vasopressin antagonist with aquaretic activity (i.e., 7-chloro-5-hydroxy-1-[2-methyl-4-(2-methylbenzoylamino)benzoyl]-2,3,4,5-tetrahydro-1H-benzazepine).

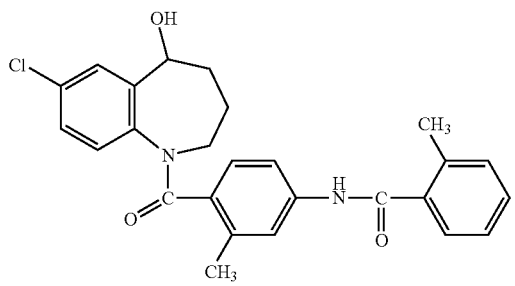

(I)

Tolvaptan contains a hydroxy-bonded carbon (5-position carbon) as an asymmetric carbon, as shown in Formula (I). Therefore, tolvaptan has a pair of optical isomers (enantiomers) based on the asymmetric carbon. The tolvaptan disclosed in Patent Literature 1 is a racemic compound, i.e., a mixture of equal amounts of the optical isomers (enantiomers) R-(+)-7-chloro-5-hydroxy-1-[2-methyl-4-(2-methylbenzoylamino)benzoyl]-2,3,4,5-tetrahydro-1H-benzazepine (hereafter, may be referred to as R-form) and S-(−)-7-chloro-5-hydroxy-1-[2-methyl-4-(2-methylbenzoylamino)benzoyl]-2,3,4,5-tetrahydro-1H-benzazepine (hereafter, may be referred to as S-form); and has an optical rotation of $[\alpha]^{20}_D=0°$. This racemic tolvaptan is sold as a therapeutic agent against fluid retention in hyponatremia and heart failure.

Processes for producing the optical isomers (R-form and S-form) of tolvaptan are disclosed in Non-patent Literature 1 to 3.

Patent Literature 2 reports that a powdered amorphous solid formulation composition obtained by spray-drying a solution containing tolvaptan and hydroxypropyl cellulose has improved solubility and improved absorbability of tolvaptan from the gastrointestinal tract.

Now, polycystic kidney disease is a hereditary disease in which multiple cysts develop in the kidneys to cause chronic kidney disease (CKD). As the disease progresses, the kidneys develop hypertrophy, leading to end stage renal disease (ESRD), which requires dialysis or transplantation. Vasopressin is believed to promote the growth of cysts, which inhibit the kidney function, in the kidneys of patients with polycystic kidney disease. Tolvaptan, a vasopressin antagonist, is attracting attention as a useful therapeutic agent for polycystic kidney disease.

CITATION LIST

Patent Literature

PTL 1: JP4-154765A
PTL 2: JP4210355B

Non Patent Literature

NPL 1: Heterocycles, 54(1), 2001, pp. 131-138
NPL 2: Heterocycles, 56, 2002, pp. 123-128
NPL 3: Tetrahedron: Asymmetry 21, (2010) 2390-2393

SUMMARY OF INVENTION

Technical Problem

As described above, a vasopressin antagonist, tolvaptan, is drawing attention as a useful therapeutic agent for polycystic kidney disease. Since tolvaptan disappears relatively rapidly when orally administered, a high dose of tolvaptan must be orally administered twice a day to steadily suppress the action of vasopressin. Further, oral administration may cause excessive diuretic effect due to the high blood concentration of tolvaptan; reduction in vasopressin antagonism due to the rapid disappearance from the blood; and the like. The high blood concentration may result in frequent urination, in particular nocturia. There is thus room for further improvement in the quality of life (QOL) of patients. Further, since patients must take a drug for their lifetimes in the treatment of polycystic kidney disease, there is a demand to reduce the frequency of administration of tolvaptan from the viewpoint of QOL and adherence of patients.

Accordingly, there is a demand for a depot formulation capable of maintaining a therapeutically effective blood concentration of tolvaptan for a long period of time in order to improve QOL and adherence of patients with polycystic kidney disease, and provide a reliable therapeutic effect. In particular, for example, a depot injection capable of maintaining vasopressin antagonism by intramuscular or subcutaneous administration every two weeks or longer, preferably every one to three months can be a very useful formulation to improve QOL and adherence of patients, and provide a reliable therapeutic effect.

An object of the present invention is to provide an injectable depot formulation of tolvaptan that is used for the prevention or treatment of polycystic kidney disease, and that can maintain a therapeutically effective blood concentration of tolvaptan for a long period of time; and a process for producing the same.

Solution to Problem

To achieve the above object, the present inventors conducted extensive research on injectable depot formulations, in particular, depot injections of tolvaptan to be administered intramuscularly or subcutaneously.

As a result, it was revealed that when an aqueous suspension of a racemic tolvaptan crystal is prepared and administered, only a low level of serum concentration can be maintained. Observation of the site of administration four weeks after the administration found that a large part of the racemic tolvaptan crystal remained unabsorbed. In the case of an aqueous suspension of a racemic tolvaptan crystal, the absorption amount of racemic tolvaptan is reduced, and a low serum concentration is maintained; therefore, efficacy cannot be expected ((1) of Test Example 4, Comparative Example 8 of FIG. 6).

However, the present inventors unexpectedly found that an injectable depot formulation comprising a particle containing optically active tolvaptan (especially, R-form or S-form) and a pharmaceutically acceptable carrier for injection can achieve the above object. More specifically, the present inventors found the following.

(1) It was found that optically active tolvaptan has higher metabolic stability than racemic tolvaptan in mammals. In rats, the R-form has higher in vitro metabolic stability than the racemic compound; in humans, the S-form has higher in vitro metabolic stability than the racemic compound (Test Example 1, (1) and (2) of FIG. 1).

(2) It was found that intramuscular administration of an aqueous suspension of optically active tolvaptan produces a higher tolvaptan serum concentration than that of racemic tolvaptan for a long period of time. In rats, the R-form produces a higher serum concentration than the racemic compound ((1) and (2) of Test Example 4, FIGS. 6 and 7).

(3) It was found that, in intramuscular administration of an aqueous suspension of optically active tolvaptan, the residual amount of tolvaptan at the site of administration four weeks after administration is lower than that of racemic tolvaptan. The residual amount indicates an amount of tolvaptan that is not absorbed at the site of administration. The above results confirmed that the absorption rate of optically active tolvaptan is faster than that of racemic tolvaptan in intramuscular administration ((1) and (2) of Test Example 4, Tables 3 and 4).

The present inventors conducted further research based on the above findings, and accomplished the present invention.

The present invention provides the following injectable depot formulation comprising optically active tolvaptan, and process for producing the same.

Item 1. An injectable depot formulation comprising:
(1) a particle containing optically active tolvaptan as an active ingredient; and
(2) a pharmaceutically acceptable carrier for injection.

Item 2. The injectable depot formulation according to item 1, wherein the optically active tolvaptan in the particle (1) is tolvaptan consisting essentially of R-tolvaptan (preferably R-tolvaptan) or tolvaptan consisting essentially of S-tolvaptan (preferably S-tolvaptan).

Item 3. The injectable depot formulation according to item 1 or 2, wherein the content of the optically active tolvaptan in the particle (1) is 50 to 100% by weight (preferably 65 to 100% by weight, more preferably 80 to 100% by weight, still more preferably 90 to 100% by weight, and particularly preferably 100% by weight).

Item 4. The injectable depot formulation according to any one of items 1 to 3, wherein the particle (1) consists essentially of the optically active tolvaptan.

Item 5. The injectable depot formulation according to any one of items 1 to 4, wherein the particle (1) has a mean particle size of about 0.2 to 100 μm (preferably 0.5 to 60 μm, and more preferably 1 to 50 μm).

Item 6. The injectable depot formulation according to any one of items 1 to 5, wherein the pharmaceutically acceptable carrier for injection (2) comprises
(a) a suspending agent and/or a wetting agent
(b) optionally, a tonicity agent and/or a bulking agent,
(c) optionally, a buffer,
(d) optionally, a pH-adjusting agent,
(e) optionally, a viscosity-enhancing agent, and
(f) optionally, a preservative.

Item 7. The injectable depot formulation according to item 6, wherein the suspending agent is sodium carboxymethyl cellulose and polyvinylpyrrolidone.

Item 8. The injectable depot formulation according to item 6 or 7, wherein the wetting agent is polysorbate 80 and/or a poloxamer.

Item 9. The injectable depot formulation according to any one of items 1 to 8, wherein the particle (1) contains a water-soluble polymer and/or a biodegradable polymer.

Item 10. The injectable depot formulation according to item 9, wherein the water-soluble polymer is at least one member selected from the group consisting of hydroxypropyl cellulose, polyvinylpyrrolidone, and hydroxypropyl methylcellulose phthalate, and the biodegradable polymer is at least one member selected from the group consisting of polylactic acids and polylactic acid-polyglycolic acid copolymers.

Item 11. The injectable depot formulation according to any one of items 1 to 10, wherein the optically active tolvaptan is amorphous.

Item 12. The injectable depot formulation according to any one of items 1 to 10, wherein the optically active tolvaptan is crystalline.

Item 13. The injectable depot formulation according to any one of items 1 to 12, which further comprises (3) water for injection and is in the form of an aqueous suspension.

Item 14. The injectable depot formulation according to item 13, wherein the concentration of the optically active tolvaptan contained in the particle (1) in the aqueous suspension is 100 mg/ml to 500 mg/ml.

Item 15. The injectable depot formulation according to any one of items 1 to 14, which is used for the prevention or treatment of polycystic kidney disease.

Item 16. The injectable depot formulation according to any one of items 1 to 15, which is administered intramuscularly or subcutaneously.

Item 17. The injectable depot formulation according to any one of items 1 to 16, which is administered once every two weeks or longer.

Item 18. A process for producing an injectable depot formulation, the process comprising mixing (1) a particle containing optically active tolvaptan as an active ingredient and (2) a pharmaceutically acceptable carrier for injection.

Item 19. A process for producing an injectable depot formulation in the form of an aqueous suspension, the process comprising mixing (1) a particle containing optically active tolvaptan as an active ingredient, (2) a pharmaceutically acceptable carrier for injection, and (3) water for injection.

Item 20. A kit for preventing or treating polycystic kidney disease, the kit comprising a container containing (1) a particle containing optically active tolvaptan as an active ingredient and (2) a pharmaceutically acceptable carrier for injection, and a container containing (3) water for injection.

Item 21. A kit for preventing or treating polycystic kidney disease, the kit comprising a container containing (1) a particle containing optically active tolvaptan as an active ingredient, and a container containing (2) a pharmaceutically acceptable carrier for injection and (3) water for injection.

Item 22. An injectable depot formulation for use in the prevention or treatment of polycystic kidney disease, the formulation comprising (1) a particle containing optically active tolvaptan as an active ingredient and (2) a pharmaceutically acceptable carrier for injection.

Item 23. An injectable depot formulation for use as a medicament for the prevention or treatment of polycystic kidney disease, the formulation comprising (1) a particle containing optically active tolvaptan as an active ingredient and (2) a pharmaceutically acceptable carrier for injection.

Item 24. Use of a combination of (1) a particle containing optically active tolvaptan as an active ingredient and (2) a pharmaceutically acceptable carrier for injection, for the production of an injectable depot formulation for preventing or treating polycystic kidney disease.

Item 25. A method for preventing or treating polycystic kidney disease, the method comprising administering an injectable depot formulation comprising (1) a particle containing optically active tolvaptan as an active ingredient and (2) a pharmaceutically acceptable carrier for injection to a patient in need of the prevention or treatment of polycystic kidney disease.

In the present specification, the term "injectable depot formulation" is used to encompass a formulation in a solid form (powders, cakes, granules, etc.) that does not comprise water for injection, and a formulation in the form of an aqueous suspension that comprises water for injection.

Advantageous Effects of Invention

The injectable depot formulation of the present invention has dissolution properties suitable as a depot formulation of optically active tolvaptan. By administering the injectable depot formulation of the present invention intramuscularly or subcutaneously, a therapeutically effective blood concentration of tolvaptan can be maintained for a long period of time.

Thus, the development of polycystic kidney disease, which is an intractable disease, can be suppressed continuously. More specifically, a therapeutically effective blood concentration of tolvaptan can be maintained or sustained by intramuscularly or subcutaneously administering the injectable depot formulation of the present invention to a patient with polycystic kidney disease every two weeks or longer, preferably every 2 to 12 weeks, and particularly preferably every two to four weeks.

The injectable depot formulation of the present invention not only has reliable therapeutic and preventive effects on symptoms of polycystic kidney disease, but also allows for convenient dosage form in which the formulation can be administered every two weeks or longer, and further suppress excessive diuretic effect. Accordingly, the injectable depot formulation of the present invention contributes to improvement in QOL of patients with polycystic kidney disease, and is extremely useful medically and industrially.

The formulation of the present invention, which comprises a particle containing optically active tolvaptan (especially, R-form or S-form), has significant effects compared to formulations comprising a particle containing racemic tolvaptan in the following points.

(1) Optically active tolvaptan has higher metabolic stability than racemic tolvaptan in mammals. In rats, the R-form has higher in vitro metabolic stability than the racemic compound; in humans, the S-form has higher in vitro metabolic stability than the racemic compound (Test Example 1, (1) and (2) of FIG. 1).

(2) Intramuscular administration or subcutaneous administration of an aqueous suspension of optically active tolvaptan produces a higher tolvaptan blood concentration than that of racemic tolvaptan. In rats, the R-form exhibits a high serum concentration ((1) and (2) of Test Example 4, FIGS. 6 and 7). This means that even if the dose of optically active tolvaptan is reduced compared to that of racemic tolvaptan, the same level of therapeutically effective blood concentration as with the racemic tolvaptan can be maintained. A long-acting formulation, when produced, commonly requires a drug to be administered at a high dose. However, since optically active tolvaptan can maintain a desired blood concentration at a lower dose, it is very useful.

(3) In intramuscular administration of an aqueous suspension of optically active tolvaptan, the residual amount of tolvaptan at the site of administration four weeks after administration is lower than that of racemic tolvaptan. The residual amount indicates an amount of tolvaptan that is not absorbed at the site of administration. The above results mean that the absorption rate of optically active tolvaptan is faster than that of racemic tolvaptan in intramuscular administration ((1) and (2) of Test Example 4, Tables 3 and 4).

The formulation comprising a particle containing amorphous optically active tolvaptan (especially, R-form or S-form) of the present invention is advantageous compared to formulations comprising a particle containing amorphous racemic tolvaptan in the following points.

(a) Intramuscular administration of an aqueous suspension of amorphous optically active tolvaptan, which has high metabolic stability, produces a higher tolvaptan serum concentration than that of amorphous racemic tolvaptan ((2) of Test Example 4, FIG. 7). This means that even if the dose of optically active tolvaptan is reduced compared to that of racemic tolvaptan, the same level of therapeutically effective blood concentration as with the racemic tolvaptan can be maintained.

(b) Amorphous optically active tolvaptan can stably maintain much higher dissolution properties than amorphous racemic tolvaptan for a long period of time (Test Example 2, FIGS. 2 to 4). This is because amorphous optically active tolvaptan is less likely to crystallize compared to amorphous racemic tolvaptan, and thus can remain amorphous.

Since amorphous optically active tolvaptan can thereby remain amorphous even when a lengthy, wet-state production process is employed, it is also useful from the standpoint of production. In addition, after administered intramuscularly or subcutaneously, amorphous optically active tolvaptan is less likely to crystallize at the site of administration, and therefore a high blood concentration can be maintained. Further, amorphous optically active tolvaptan, when formulated into an aqueous suspension for administration to a patient in clinical settings, can remain amorphous for a long period of time; therefore, it is not necessary to administer the formulation immediately after preparation.

(c) The residual amount of amorphous optically active tolvaptan at the site of administration four weeks after administration is lower than that of amorphous racemic tolvaptan ((2) of Test Example 4, Table 4).

The formulation comprising a particle containing crystalline optically active tolvaptan (especially, R-form or S-form) of the present invention is advantageous compared to formulations comprising a particle containing crystalline racemic tolvaptan in the following points.

(i) Intramuscular administration or subcutaneous administration of an aqueous suspension of crystalline optically active tolvaptan, which has high metabolic stability, produces a higher tolvaptan blood concentration than that of crystalline racemic tolvaptan (e.g., (1) of Test Example 4, FIG. 6).

(ii) Crystalline optically active tolvaptan can stably maintain higher dissolution properties than crystalline racemic tolvaptan for a long period of time. The dissolution rate of crystalline racemic form decreases, whereas the dissolution rate of crystalline optically active form is stably maintained (Test Example 3, FIG. 5).

Since crystalline optically active tolvaptan can thereby remain crystalline even when a lengthy, wet-state production process is employed, it is also useful from the standpoint of production. In addition, the dissolution rate of crystalline optically active tolvaptan does not decrease compared to that of crystalline racemic tolvaptan. Further, there is no concern regarding decrease in the dissolution rate when crystalline optically active tolvaptan is formulated into an aqueous suspension for administration to a patient in clinical settings; therefore, it is not necessary to administer the formulation immediately after preparation.

(iii) The residual amount of crystalline optically active tolvaptan at the site of administration four weeks after administration is lower than that of crystalline racemic tolvaptan ((1) of Test Example 4, Table 3). The residual amount indicates an amount of tolvaptan that is not absorbed at the site of administration. The above results mean that the absorption rate of crystalline optically active tolvaptan is faster than that of crystalline racemic tolvaptan in intramuscular administration. In addition, a higher tolvaptan blood concentration can be maintained in crystalline optically active tolvaptan compared to crystalline racemic tolvaptan.

The formulation comprising a particle containing crystalline optically active tolvaptan (especially, R-form or S-form) of the present invention is advantageous compared to formulations comprising a particle containing amorphous optically active tolvaptan in the following points.

(I) In crystalline optically active tolvaptan, a high serum concentration immediately after administration (initial burst, etc.) as found in amorphous optically active tolvaptan is not observed, and a therapeutically effective serum concentration can be maintained at a constant level for a long period of time. Because of less fluctuation of serum concentration, excessive diuresis associated with the high blood concentration can be inhibited ((3) of Test Example 4, FIG. 8).

(II) Crystalline optically active tolvaptan produces a higher serum concentration from day 14 after administration than amorphous optically active tolvaptan, and is preferably formulated into a depot injection to be administered every four weeks or longer ((3) of Test Example 4, FIG. 8).

It was confirmed that the formulation comprising a particle containing crystalline optically active tolvaptan (especially, R-form or S-form) of the present invention can suppress increase in kidney weight or kidney volume, and maintain a constant effective plasma concentration of tolvaptan for a long period of time in polycystic kidney disease model animals (Test Examples 5 and 6, Tables 7 and 8, FIGS. 9 and 10). These results show that the formulation is useful for the prevention or treatment of polycystic kidney disease in mammals including humans.

DESCRIPTION OF EMBODIMENTS

1. Injectable Depot Formulation

Figure 1:
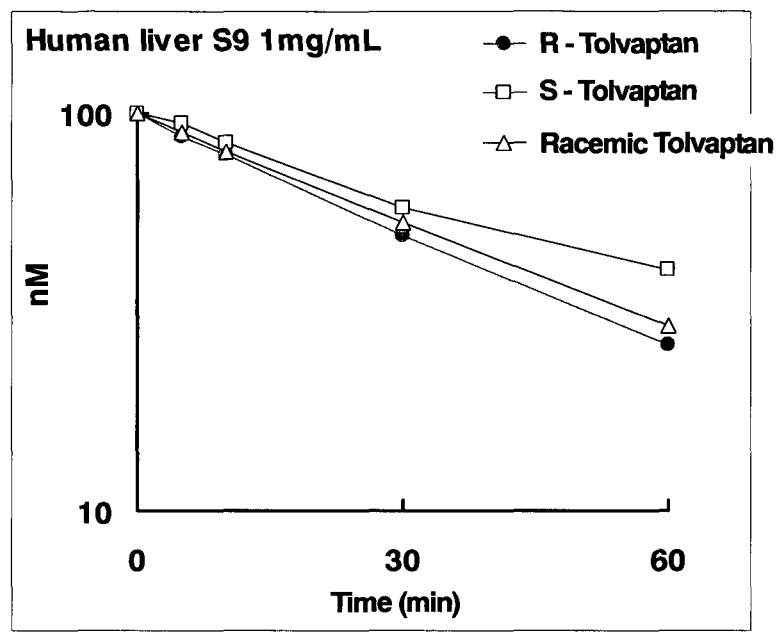
FIG. 1 shows the results of a test of metabolic stability of racemic tolvaptan and optically active tolvaptan (R-form and S-form) in Test Example 1. The test used human and rat liver homogenates (S9 fractions). The circle indicates the R-form, the square indicates the S-form, and the triangle indicates the racemic compound.
Figure 1:
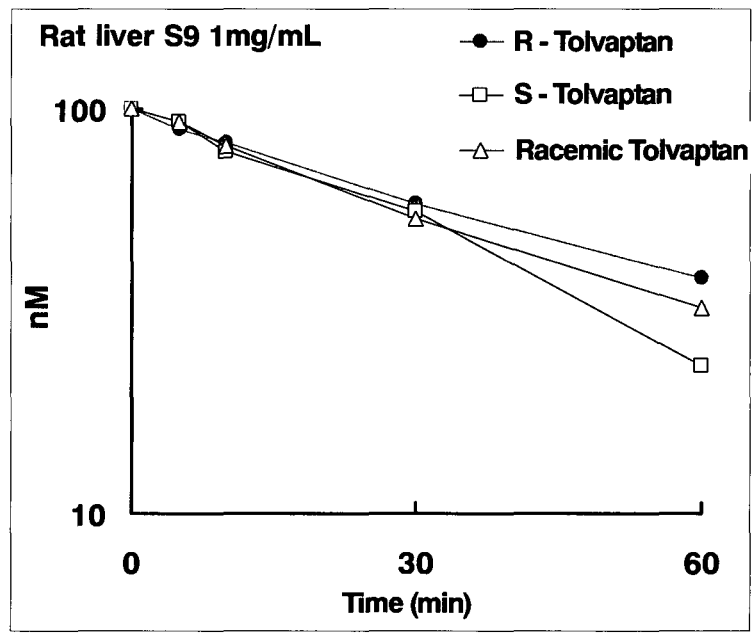

The injectable depot formulation of the present invention comprises (1) a particle containing optically active tolvaptan as an active ingredient and (2) a pharmaceutically acceptable carrier for injection. The injectable depot formulation of the present invention encompasses a formulation in a solid form (powders, cakes, granules, etc.) that does not comprise water for injection, and a formulation in the form of an aqueous suspension that comprises water for injection.

Each ingredient of the formulation of the present invention is described below.

(1) Particle Containing an Active Ingredient

Optically Active Tolvaptan

The particle containing an active ingredient of the present invention contains tolvaptan as an active ingredient, and the tolvaptan is optically active tolvaptan.

The term "optically active tolvaptan" means tolvaptan consisting essentially of R-(+)-7-chloro-5-hydroxy-1-[2-methyl-4-(2-methylbenzoylamino)benzoyl]-2,3,4,5-tetrahydro-1H-benzazepine (R-tolvaptan) or tolvaptan consisting essentially of S-(−)-7-chloro-5-hydroxy-1-[2-methyl-4-(2-methylbenzoylamino)benzoyl]-2,3,4,5-tetrahydro-1H-benzazepine (S-tolvaptan).

Optically active tolvaptan can be produced based on the disclosures of, for example, Non-patent Literature 1, Non-patent Literature 2, Non-patent Literature 3, or the like.

The term "tolvaptan consisting essentially of R tolvaptan" means tolvaptan that may contain its enantiomer, S-form, as long as the effect of the present invention is achieved. More specifically, the term "tolvaptan consisting essentially of R-tolvaptan" means tolvaptan having an optical purity (enantiomeric excess: ee) of R-form of generally not less than 80% ee, preferably not less than 90% ee, more preferably not less than 95% ee, still more preferably not less than 99% ee, and particularly preferably 100% ee. That is, enantiopure R-tolvaptan is preferable.

The term "tolvaptan consisting essentially of S-tolvaptan" means tolvaptan that may contain its enantiomer, R-form, as long as the effect of the present invention is achieved. More specifically, the term "tolvaptan consisting essentially of S-tolvaptan" means tolvaptan having an optical purity (enantiomeric excess: ee) of S-form of generally not less than 80% ee, preferably not less than 90% ee, more preferably not less than 95% ee, still more preferably not less than 99% ee, and particularly preferably 100% ee. That is, enantiopure S-tolvaptan is preferable.

From the viewpoint of high absorbability and high metabolic stability in humans, tolvaptan consisting essentially of S-tolvaptan is preferable, and S-tolvaptan is more preferable.

Optically active tolvaptan encompasses anhydrides, solvates (e.g., hydrates, alcoholates, etc.), co-crystals, and the like of the tolvaptan. Further, optically active tolvaptan encompasses those in which one or more atoms in the tolvaptan molecule are replaced by one or more isotopic atoms. Examples of isotopic atoms include deuterium ($^2$H), tritium ($^3$H), $^{13}$C, $^{14}$N, $^{18}$O, and the like.

Optically active tolvaptan may be crystalline or amorphous.

The term "amorphous" in "amorphous optically active tolvaptan" indicates that the content of crystalline tolvaptan based on total tolvaptan content of the particle is less than 10% by weight, preferably less than 5% by weight, more preferably less than 3% by weight; and particularly preferably indicates that no crystalline tolvaptan is detected.

The term "crystalline" in "crystalline optically active tolvaptan" indicates that the content of crystalline tolvaptan based on total tolvaptan content of the particle is not less than 90% by weight, preferably not less than 95% by weight, more preferably not less than 97% by weight; and particularly preferably indicates that no amorphous tolvaptan is detected.

The content of crystalline tolvaptan based on total tolvaptan content of the particle can be determined by measuring the particle using an analyzer such as an X-ray diffractometer, differential scanning calorimeter (DSC), near infrared (NIR) spectrometer, microcalorimeter, Raman spectrometer, or terahertz spectrometer.

Particle

The particle containing the active ingredient, i.e., optically active tolvaptan, encompasses a particle containing optically active tolvaptan and one or more other ingredients, and a particle consisting essentially of optically active tolvaptan (including a particle consisting of optically active tolvaptan).

Examples of other ingredients include those that are added to control the release rate of optically active tolvaptan from the particle. Examples of other ingredients include a water-soluble polymer and/or a biodegradable polymer.

Examples of water-soluble polymers include polyvinylpyrrolidone (PVP), hydroxypropyl cellulose (HPC), hydroxypropyl methylcellulose phthalate (HPMCP), hydroxypropyl methylcellulose (HPMC), methacrylic acid copolymer L, methylcellulose (MC), and the like. Preferable water-soluble polymers are hydroxypropyl cellulose (HPC), polyvinylpyrrolidone (PVP), and hydroxypropyl methylcellulose phthalate (HPMCP).

Examples of biodegradable polymers include polylactic acids, polyglycolic acids, polycaprolactones, polycarbonates, polyester amides, polyanhydrides, polyamino acids, polyorthoesters, polycyanoacrylates, poly(p-dioxanone)s, poly(alkylene oxalate)s, biodegradable polyurethanes, mixtures thereof, and copolymers thereof. If the polymers contain asymmetric carbon atoms, monomers constituting the polymers may be any of D-form, L-form, or DL-form. L-form is preferable. Preferable biodegradable polymers are polylactic acids and polylactic acid-polyglycolic acid copolymers.

The weight ratio of the optically active tolvaptan to the water-soluble polymer and/or the biodegradable polymer in the particle is generally 1:0 to 1:4, further 4:1 to 1:4, furthermore 4:1 to 1:2, and particularly 2:1 to 1:1. In particular, it is suitable that the weight ratio of the optically active tolvaptan to the water-soluble polymer and/or the biodegradable polymer in the particle is 1:0.

The content of optically active tolvaptan in the particle containing optically active tolvaptan is generally 50 to 100% by weight, preferably 65 to 100% by weight, more preferably 80 to 100% by weight, still more preferably 90 to 100% by weight, and particularly preferably 100% by weight.

The content of optically active tolvaptan in the particle consisting essentially of optically active tolvaptan is generally 80 to 100% by weight, preferably 90 to 100% by weight, more preferably 95 to 100% by weight, still more preferably 98 to 100% by weight, and particularly preferably 100% by weight.

The mean particle size of the particle containing optically active tolvaptan can generally be set to 0.2 to 100 μm, preferably 0.5 to 60 μm, and more preferably 1 to 50 μm. The mean particle size of the particle is a volume mean diameter, and can be determined using a laser diffraction particle size distribution meter.

In particular, a particle containing amorphous optically active tolvaptan is generally prepared by dissolving optically active tolvaptan together with, if necessary, a water-soluble polymer and/or a biodegradable polymer in an organic solvent, and then spray-drying the mixture. Thus, the particle generally has a spherical shape. The mean particle size of the particle can be set within a desired range (0.2 to 100 μm, preferably 2 to 60 μm, more preferably 4 to 50 μm) by suitably changing the conditions of the spray-drying method.

A particle containing crystalline optically active tolvaptan is prepared, for example, by recrystallizing optically active tolvaptan synthesized based on Non-patent Literature 1 to 3, or the like. The particle is prepared so as to have a desired mean particle size by a known pulverization method, preferably wet pulverization. The mean particle size of the particle can be set within a desired range (0.2 to 100 μm, preferably 0.5 to 30 μm, more preferably 1 to 10 μm) by suitably changing the conditions of the pulverization.

Figure 6:
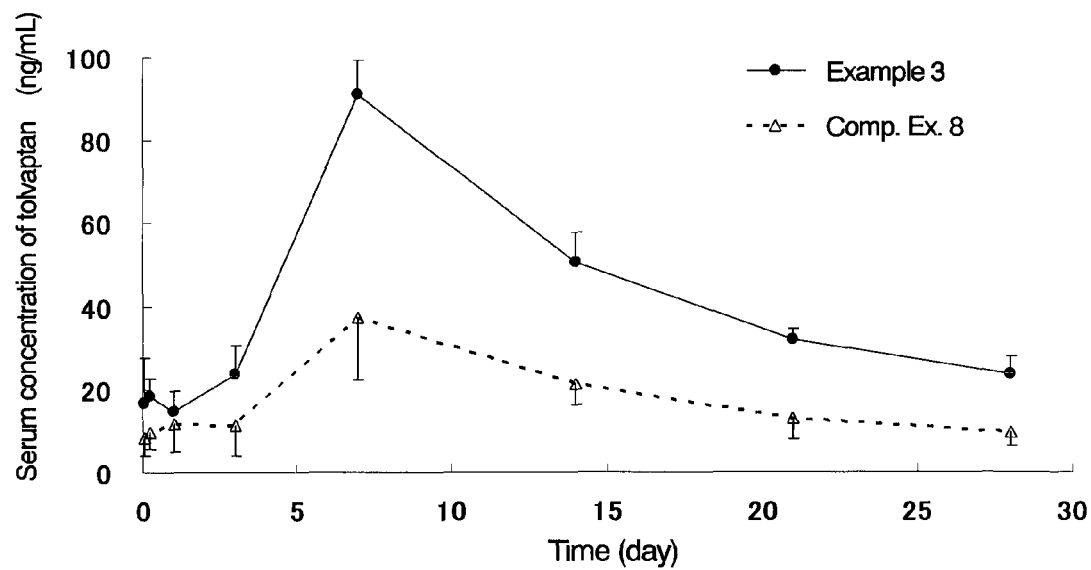
FIG. 6 shows profiles of serum concentration of tolvaptan when an aqueous suspension containing a crystalline R-tolvaptan particle (Example 3) and an aqueous suspension containing a crystalline racemic tolvaptan particle (Comparative Example 8) are each individually administered intramuscularly in an amount of 100 mg/kg to female rats in (1) of Test Example 4.
Figure 7:
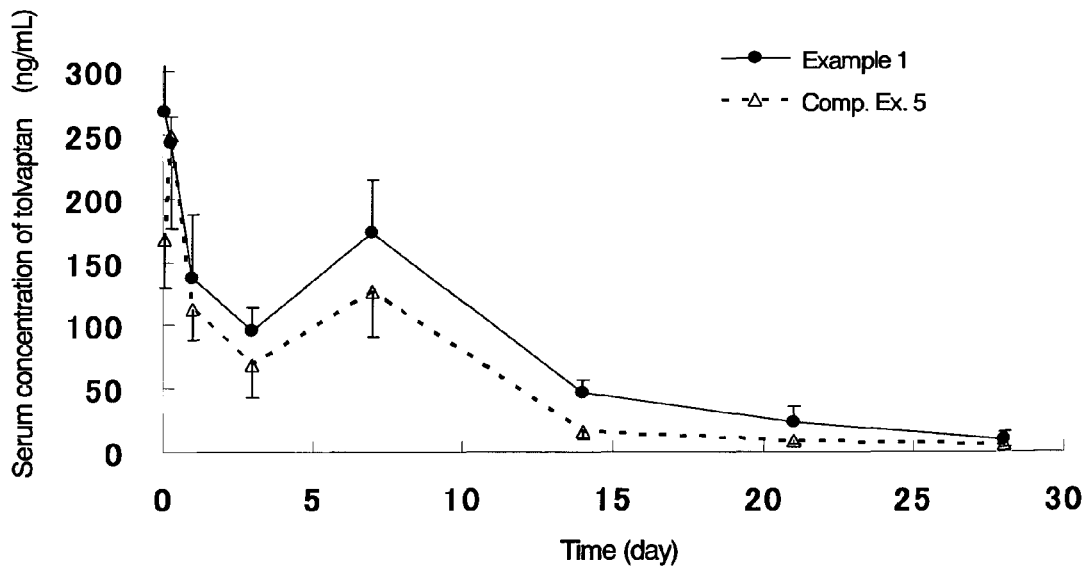
FIG. 7 shows profiles of serum concentration of tolvaptan when an aqueous suspension containing an amorphous R-tolvaptan powder (Example 1) and an aqueous suspension containing an amorphous racemic tolvaptan powder (Comparative Example 5) are each individually administered intramuscularly in an amount of 100 mg/kg to female rats in (2) of Test Example 4.

When a particle containing amorphous optically active tolvaptan is used (Examples 1 and 2), high dissolution properties can be maintained for a long period of time (Test Example 2, FIG. 4), and a high blood concentration can be maintained for a long period of time in intramuscular administration or subcutaneous administration (e.g., (1) and (2) of Test Example 4, FIGS. 6 and 7, Example 1 and Comparative Ex. 8), compared to when a particle containing crystalline racemic tolvaptan (Comparative Example 7) is used. This enables the development of cystic kidney to be effectively suppressed in polycystic kidney disease.

In particular, it should be noted that amorphous optically active tolvaptan can maintain much higher dissolution properties for a long period of time than amorphous racemic tolvaptan. More specifically, the dissolution test results shown in FIGS. 2 to 4 reveal that the high dissolution amounts are maintained for a long period of time after the start of dissolution (140 hours, about 6 days) in the case of the formulations of Example 1 (R-form) and Example 2 (S-form), whereas the dissolution amounts are significantly decreased in a relatively short period of time in the case of the formulations of Comparative Examples 1 to 6 (racemic compound). This is believed to be because the amorphous optically active tolvaptan of Examples 1 and 2 is much less likely to crystallize than amorphous racemic tolvaptan, and therefore the high dissolution amounts can be maintained. Accordingly, the amorphous optically active tolvaptan in the particle containing amorphous optically active tolvaptan is useful from the standpoint of producing a formulation since it can remain amorphous even in a process involving a wet-state step (e.g., wet pulverization) that takes a relatively long period of time. In addition, a high blood concentration can be maintained in intramuscular or subcutaneous administration since the amorphous optically active tolvaptan is less likely to crystallize after the administration. Further, the amorphous optically active tolvaptan, when formulated into an aqueous suspension for administration to a patient in clinical settings, can also remain amorphous for a long period of time, and is therefore clinically useful.

Figure 5:
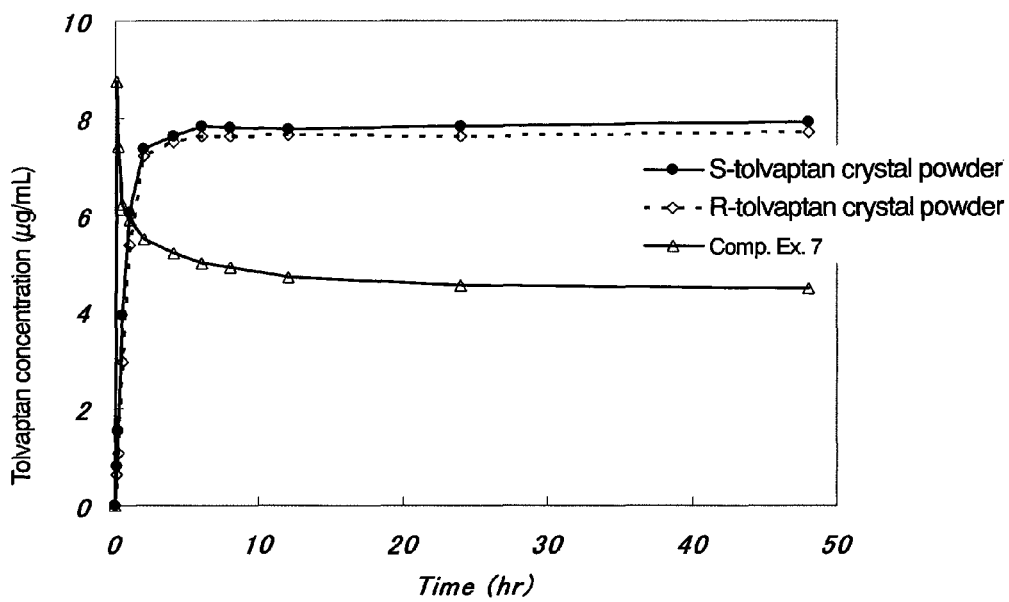
FIG. 5 shows the results of a dissolution test for an R-tolvaptan crystal powder, an S-tolvaptan crystal powder, and the crystalline racemic tolvaptan powder of Comparative Example 7 in Test Example 3.

It should be noted that crystalline optically active tolvaptan (R-form or S-form) has dissolution properties more stable than crystalline racemic tolvaptan (Comparative Example 7) (FIG. 5). It should also be noted that when crystalline optically active tolvaptan, which has excellent absorbability and metabolic stability is used in intramuscular administration or subcutaneous administration, a high blood concentration can be maintained for a long period of time compared to when crystalline racemic tolvaptan is used (e.g., FIG. 6, Example 3 and Comparative Example 8). This allows the development of cystic kidney to be effectively suppressed in polycystic kidney disease. Additionally, in crystalline optically active tolvaptan, a high blood concentration immediately after administration (initial burst) is not observed, unlike in amorphous racemic tolvaptan and amorphous optically active tolvaptan; and a therapeutically effective blood concentration can be maintained for a long period of time (e.g., FIGS. 7 and 8 of Test Example 4). This inhibits excessive diuretic effect. Crystalline optically active tolvaptan is thus useful for QOL and adherence of patients.

Further, since crystalline optically active tolvaptan can by nature maintain an excellent blood concentration for a long period of time in the crystalline state, it is not necessary to consider the issue of crystallization from an amorphous state in an aqueous suspension. Thus, crystalline optically active tolvaptan is advantageous in terms of clinically extremely excellent handleability. Further, optically active tolvaptan crystals do not show decrease in the dissolution rate compared to racemic tolvaptan crystals. Accordingly, since the crystalline form can be maintained for a long period of time, the fluctuation of blood concentration is small, and a therapeutically effective blood concentration can be maintained for a long period of time.

(2) Pharmaceutically Acceptable Carrier for Injection

The pharmaceutically acceptable carrier for injection is used for formulating the particle containing the active ingredient, i.e., optically active tolvaptan, into an aqueous suspension. The carrier for injection generally comprises (a) a suspending agent and/or a wetting agent, (b) optionally, a tonicity agent and/or a bulking agent, (c) optionally, a buffer, (d) optionally, a pH-adjusting agent, (e) optionally a viscosity-enhancing agent, and (f) optionally, a preservative.

The suspending agent and/or wetting agent (a) is essential for suspending the optically active tolvaptan in water.

Examples of suitable suspending agents include sodium carboxymethyl cellulose, hydroxypropyl cellulose, carboxymethyl cellulose, hydroxypropylethyl cellulose, methylcellulose, hydroxypropylmethyl cellulose, polyvinyl alcohol, macrogol, polyvinylpyrrolidone, and the like. They may be used singly, or in a combination of two or more. In particular, a combination of sodium carboxymethyl cellulose and polyvinylpyrrolidone is preferable.

The amount of the suspending agent to be contained is within the range of generally about 0.1 to about 10 w/v %, and preferably about 0.2 to about 5 w/v %, based on the total volume of the injectable formulation (aqueous suspension containing water for injection).

Examples of suitable wetting agents include various surfactants (including nonionic and ionic surfactants), such as gelatin, lecithin (phosphatides), sorbitan esters, polyoxyethylene alkyl ethers, polyoxyethylene castor oil derivatives, polyoxyethylene sorbitan fatty acid esters (e.g., commercially available Tweens (registered trademark); for example, Tween 20 (registered trademark) and Tween 80 (registered trademark, polysorbate 80) (ICI Specialty Chemicals)), poloxamers (e.g., Pluronic F-68 (registered trademark) and Pluronic F-108 (registered trademark), which are block copolymers of ethylene oxide and propylene oxide); and poloxamines (e.g., Tetronic 908 (registered trademark), also known as Poloxamine 908 (registered trademark) which is a tetrafunctional block copolymer derived from sequential addition of propylene oxide and ethylene oxide to ethylenediamine (BASF Wyandotte Corporation, Parsippany, N.J.)). They may be used singly, or in a combination of two or more. In particular, polysorbate 80 and poloxamers are preferable.

The amount of the wetting agent to be contained is within the range of generally about 0.01 to about 5 w/v %, and preferably about 0.1 to about 2 w/v %, based on the total volume of the injectable formulation.

The carrier for injection may comprise (b) a tonicity agent and/or a bulking agent, if necessary. Examples of tonicity agents include sodium chloride, potassium chloride, mannitol, sucrose, lactose, maltose, xylitol, glucose, sorbitol, and the like. They may be used singly, or in a combination of two or more.

When the carrier for injection comprises a tonicity agent and/or a bulking agent, the amount of the tonicity agent and/or the bulking agent to be contained is within the range of generally about 0.2 to about 12 w/v %, and preferably about 0.5 to about 10 w/v % based on the total volume of the injectable formulation.

The carrier for injection may comprise (c) a buffer, if necessary. Examples of buffers suitable in the present invention include sodium citrate, sodium tartrate, sodium phosphate, potassium phosphate, Tris buffer, and the like. They may be used singly, or in a combination of two or more. In particular, sodium phosphate (in particular, sodium dihydrogen phosphate) is preferable.

When the carrier for injection comprises a buffer, the amount of the buffer to be contained is an amount sufficient to adjust the pH of the aqueous suspension prepared at the time of use to generally about 6 to about 8, and preferably about 7. To achieve such a pH, the buffer, depending on the type, is generally used in an amount within the range of about 0.02 to about 2% by weight, preferably about 0.03 to about 1% by weight, and more preferably about 0.1% by weight, based on the total weight of the injectable formulation.

The carrier for injection may comprise (d) a pH-adjusting agent, if necessary. The pH-adjusting agent is used in an amount sufficient to adjust the pH of the aqueous suspension prepared at the time of use within the range of about 6 to about 8, and preferably about 7; and may be a base or acid depending upon whether the pH of the aqueous suspension of tolvaptan must be raised or lowered to adjust the pH to the desired neutral pH of about 7. Thus, when the pH must be lowered, an acidic pH-adjusting agent (such as hydrochloric acid, phosphoric acid, and acetic acid, preferably hydrochloric acid) may be used. When the pH must be raised, a basic pH-adjusting agent (such as sodium hydroxide, potassium hydroxide, calcium carbonate, magnesium oxide, and magnesium hydroxide, preferably sodium hydroxide) may be used.

The carrier for injection may comprise (e) a viscosity-enhancing agent, if necessary. Examples of viscosity-enhancing agents include sodium carboxymethyl cellulose, and the like.

The carrier for injection may comprise (f) a preservative, if necessary. Examples of preservatives include quaternary ammonium salts, such as benzalkonium chloride and benzethonium chloride; cationic compounds, such as chlorhexidine gluconate; p-hydroxybenzoates, such as methyl parahydroxybenzoate, ethyl parahydroxybenzoate, and propyl parahydroxybenzoate; alcohol compounds such as chlorobutanol and benzyl alcohol; sodium dehydroacetate; thimerosal; and the like.

The present invention provides an injectable depot formulation that comprises (1) a particle containing optically active tolvaptan as an active ingredient and (2) a pharmaceutically acceptable carrier for injection (and further (3) water for injection, if necessary), for use in the prevention or treatment of polycystic kidney disease.

The present invention provides use of a combination of (1) a particle containing optically active tolvaptan as an active ingredient and (2) a pharmaceutically acceptable carrier for injection (and further (3) water for injection, if necessary), for the production of an injectable depot formulation for preventing or treating polycystic kidney disease.

The present invention also provides a method for preventing or treating polycystic kidney disease that comprises administering an injectable depot formulation comprising (1) a particle containing optically active tolvaptan as an active ingredient and (2) a pharmaceutically acceptable carrier for injection (and further (3) water for injection, if necessary) to a patient in need of the prevention or treatment of polycystic kidney disease.

2. Preparation of the Formulation of the Present Invention

The injectable depot formulation of the present invention can be prepared by mixing (1) a particle containing optically active tolvaptan as an active ingredient and (2) a pharmaceutically acceptable carrier for injection.

The injectable depot formulation in the form of an aqueous suspension of the present invention can be prepared by mixing (1) a particle containing optically active tolvaptan as an active ingredient, (2) a pharmaceutically acceptable carrier for injection, and (3) water for injection.

In each process above, the amount of optically active tolvaptan to be contained in the particle (1) may be a therapeutically effective amount, and is appropriately adjusted according to the purpose.

A particle containing amorphous optically active tolvaptan can be prepared, for example, by dissolving optically active tolvaptan together with, if necessary, a water-soluble polymer and/or a biodegradable polymer in an organic solvent; distilling the organic solvent off; and obtaining powder. An organic solvent that can dissolve each ingredient and be easily distilled off is selected. Examples of organic solvents include methylene chloride, and mixed solvents of methylene chloride and alcohol (methanol or ethanol). A particle with a desired particle size distribution can be produced by spray-drying the obtained solution. The process for producing the particle can be performed, for example, according to the process described in Patent Literature 2 (JP4210355B).

A particle containing crystalline optically active tolvaptan (in particular, a particle consisting essentially of crystalline optically active tolvaptan) can be prepared, for example, by recrystallizing optically active tolvaptan, and pulverizing the recrystallized optically active tolvaptan into powder. The process for producing the particle can be performed, for example, using a commonly used dry mill (jet mill, hammer mill, or the like). As other examples of the process for producing the particle, controlled crystallization method, etc., can be mentioned. For example, the particle can be prepared by dissolving tolvaptan in an organic solvent (good solvent), followed by precipitation with a poor solvent such as water. A particle containing crystalline optically active tolvaptan and one or more other ingredients (e.g., the above-described water-soluble polymer and/or biodegradable polymer) can be prepared, for example, by dissolving the one or more other ingredients in a solvent in which a particle of crystalline optically active tolvaptan is practically insoluble, suspending the particle of crystalline optically active tolvaptan in the solution, and wet-pulverizing the particle. A wet pulverization technique, such as wet ball milling, high-pressure homogenization, and high-shear homogenization, is preferably used. In addition to these pulverization techniques, a low-energy or high-energy mill (for example, a roller mill) can also be used. The particle containing crystalline optically active tolvaptan and one or more other ingredients can be prepared by spray-drying the suspension.

The injectable depot formulation in a solid form of the present invention can be prepared by mixing the particle (1) and the pharmaceutically acceptable carrier for injection (2) at a predetermined ratio.

When the injectable depot formulation of the present invention is in the form of an aqueous suspension, it can be generally prepared by mixing the particle (1), the pharmaceutically acceptable carrier for injection (2), and water for injection (3) at a predetermined ratio.

For example, the aqueous suspension can also be prepared by mixing the particle (1) and an aqueous solution containing the pharmaceutically acceptable carrier for injection (2) and water for injection (3).

More specifically, for example, an aqueous solution containing a pharmaceutically acceptable carrier for injection (2) and water for injection (3) is mixed with a sterile particle containing optically active tolvaptan (1) enclosed in a container, such as a vial; the mixture thus obtained is subsequently, for example, shaken vigorously, stirred with a vortex mixer, or subjected to ultrasonic irradiation, thereby preparing a homogeneous aqueous suspension. A homogeneous aqueous suspension can also be prepared by providing two sterile syringes, enclosing a sterile particle containing optically active tolvaptan (1) in one of the syringes, placing an aqueous solution containing a pharmaceutically acceptable carrier for injection (2) and water for injection (3) in the other syringe, connecting the two syringes by a connector, and performing pumping repeatedly. An aqueous suspension can be prepared using any of the above processes at the time of use.

When any of the preparation processes described above are employed, the formulation of the present invention may be, for example, in the form of a kit for preventing or treating polycystic kidney disease that comprises a container containing (1) a particle containing optically active tolvaptan as an active ingredient and a container containing (2) a pharmaceutically acceptable carrier for injection and (3) water for injection.

As another example, the aqueous suspension can be prepared by adding water for injection (3) to a formulation in a solid form that does not comprises water for injection (3) (i.e., a solid formulation comprising the particle (1) and the pharmaceutically acceptable carrier for injection (2)) at the time of use.

When the preparation processes described above are employed, the formulation of the present invention may be, for example, in the form of a kit for preventing or treating polycystic kidney disease that comprises a container containing (1) a particle containing optically active tolvaptan as an active ingredient and (2) a pharmaceutically acceptable carrier for injection, and a container containing (3) water for injection.

As the above-described ingredients and the amounts thereof to be contained, the ingredients and amounts (including a predetermined ratio, etc.) described in the section "1. Injectable depot formulation" above can be used.

3. Administration Method (Usage and Dosage)

The injectable depot formulation of the present invention can be used for prevention or treatment of polycystic kidney disease. The formulation is prepared by mixing (1) a particle containing optically active tolvaptan, (2) a pharmaceutically acceptable carrier for injection, and (3) water for injection under sterile conditions to produce an aqueous suspension that is homogeneous, after which the formulation can be administered intramuscularly or subcutaneously via injection to a patient who requires prevention or treatment of polycystic kidney disease. The aqueous suspension can be also produced at the time of use.

Unlike the particle containing amorphous racemic tolvaptan, when the particle (1) contains amorphous optically active tolvaptan, crystallization is not likely to occur in the aqueous suspension (Test Example 2, FIGS. 2 to 4); therefore, the high dissolution amount is maintained for a long period of time. Thus, since a formulation containing a particle that includes amorphous optically active tolvaptan ensures sufficient stability during the period after the preparation of a tolvaptan aqueous suspension, for example, in the pharmaceutical department of a hospital until administration to a patient, it is clinically extremely useful. Further, since crystallization is not likely to occur at an administration site, a high blood concentration can be maintained for a long period of time compared to amorphous racemic tolvaptan.

When the particle (1) includes crystalline optically active tolvaptan, since the optically active tolvaptan is originally crystalline, it is not necessary to consider the problem of amorphous-to-crystalline transformation of tolvaptan in the aqueous suspension. Therefore, such a particle has an advantage of being clinically extremely easy to handle. The crystalline optically active tolvaptan is clinically extremely easy to handle because it shows no dissolution rate reduction compared to a racemic crystal (Test Example 3, FIG. 5). Moreover, since the crystalline optically active tolvaptan can remain crystalline for a long period of time after administration, change in serum concentration is small compared to amorphous optically active tolvaptan (Test Example 4 (3) and FIG. 8), and a high serum concentration can be maintained for a long period of time compared to a racemic crystal. For this reason, an optically active tolvaptan crystal is most preferable (Test Example 4 (1) and FIG. 6).

When the injectable depot formulation of the present invention is an aqueous suspension, the amount (concentration) of tolvaptan contained in the aqueous suspension is not particularly limited as long as it is a therapeutically effective amount. Therapeutically effective amount indicates an amount that improves clinical symptom. The amount (concentration) of optically active tolvaptan in the aqueous suspension is preferably adjusted to within the range of 100 mg/mL to 500 mg/mL, and more preferably 200 mg/mL to 400 mg/mL. The amount of the aqueous suspension intramuscularly or subcutaneously administered to a patient per each is generally 0.5 mL to 6 mL, and preferably 1 mL to 3 mL.

The amount of the optically active tolvaptan described above also indicates an amount of tolvaptan in the aqueous suspension prepared by constituting the solid formulation with water for injection, etc.

The dosage actually used depends on a patient. For example, when a formulation is administered every two weeks, tolvaptan is preferably administered at a dose of 100 to 1000 mg in one or two administrations; and when a formulation is administered every four weeks, tolvaptan is preferably administered at a dose of 200 to 2000 mg in one or two to four administrations. When a formulation is administered every eight weeks, tolvaptan is preferably administered at a dose of 400 to 4000 mg in one or two to four administrations; and when a formulation is administered every 12 weeks, tolvaptan is preferably administered at a dose of 600 to 6000 mg in one or two to four administrations. When a formulation is administered with a longer administration interval, the particle (1) is preferably a particle containing crystalline optically active tolvaptan because a high blood concentration can be maintained for a long period of time.

There are two types of optical active tolvaptan, i.e., R-form and S-form. For example, when a particle containing R-tolvaptan is administered to a rat or rabbit, and when a particle containing S-tolvaptan is administered to a dog or human, a high blood concentration can be maintained compared to when a particle containing a racemic compound is used, making it possible to reduce the dosage amount. In general, since local irritation at an administration site is known to depend on a single dose, a reduction in the single dose can lower the local irritation at an administration site. Further, since crystalline S-tolvaptan has high metabolic stability in human, the effective blood concentration can be kept constant, which is preferable.

EXAMPLES

The present invention will now be illustrated with the following examples. However, the invention is not limited thereto or thereby.

Example 1

Preparation of R-Tolvaptan Spray-Dried (SD) Powder Containing 33% HPC-SL

An R-tolvaptan crystal (100.6 g, produced by Otsuka pharmaceutical Co., Ltd.) and hydroxypropyl cellulose (50.3 g, HPC-SL, produced by Nippon Soda Co., Ltd.) were dissolved in dichloromethane (1055 mL) and ethanol (455 mL). Using a spray dryer (Pulvis GB21, produced by Yamato Scientific Co., Ltd.), the solution was spray-dried at a spray pressure of 1.6 to 1.7 kg/cm$^2$, a heater temperature of 60° C., and a liquid sending speed of 10 to 15 g/min. The prepared spray-dried powder was dried under reduced pressure. In the powder X-ray diffraction of the prepared powder, only a halo peak was observed. Thus, the prepared powder was confirmed to be amorphous.

The R-tolvaptan SD powder (300 mg) was loaded into a syringe, and a medium solution (0.76 g) shown below (Table 1) was loaded into the other syringe. The two syringes were connected via a connector. Pumping was performed repeatedly to prepare 200 mg/mL of a homogeneous amorphous R-tolvaptan aqueous suspension. The mean particle size of the R-tolvaptan SD powder measured using a laser diffraction particle size distribution meter (SALD-3000J, produced by Shimadzu Corporation) according to a wet process was 5.8 μm.

TABLE 1

| Composition of medium solution (per mL of formulation) | |
| --- | --- |
| | Prescribed amount |
| Polysorbate 80 | 1.00 mg |
| Sodium carboxymethyl cellulose | 10.0 mg |
| D-mannitol | 35.0 mg |
| Sodium dihydrogen phosphate monohydrate | 0.74 mg |
| Sodium hydroxide | q.s. to pH 7.0 |
| Water for injection | q.s. to 1 mL |
| Total weight | 0.83 g |

Example 2

Preparation of S-Tolvaptan Spray-Dried (SD) Powder Containing 33% HPC-SL

An S-tolvaptan crystal (100.3 g, produced by Otsuka pharmaceutical Co., Ltd.) and hydroxypropyl cellulose (50.3 g, HPC-SL, Nippon Soda Co., Ltd.) were dissolved in dichloromethane (1050 mL) and ethanol (450 mL). Using a spray dryer (Pulvis GB21, produced by Yamato Scientific Co., Ltd.), the solution was spray-dried at a spray pressure of 1.7 kg/cm$^2$, a heater temperature of 60° C., and a liquid sending speed of 10 to 15 g/min. The prepared spray-dried powder was dried under reduced pressure. In the powder X-ray diffraction of the prepared powder, only a halo peak was observed. Thus, the prepared powder was confirmed to be amorphous.

The S-tolvaptan SD powder (300 mg) was loaded into a syringe, and the medium solution (0.76 g) of Example 1 (Table 1) was loaded into the other syringe. The two syringes were connected via a connector. Pumping was performed repeatedly to prepare 200 mg/mL of a homogeneous amorphous S-tolvaptan aqueous suspension.

The mean particle size of the S-tolvaptan SD powder measured using a laser diffraction particle size distribution meter (SALD-3000J, produced by Shimadzu Corporation) according to a wet process was 6.2 μm.

Example 3

R-Tolvaptan Crystal Particle Formulation

An R-tolvaptan crystal (2.0 g, produced by Otsuka pharmaceutical Co., Ltd.) was suspended in the medium solution of Example 1 (Table 1) (8.3 g) (equal to 10 mL). Zirconia beads (10 g) having a diameter of 1.5 mm were added to the suspension. A stirring bar was introduced into a container, and stirring was performed using a stirrer to perform bead pulverization (wet pulverization), thereby preparing 200 mg/mL of a homogeneous R-tolvaptan crystal aqueous suspension. The mean particle size of the R-tolvaptan crystal particle measured during ultrasonic irradiation using a laser diffraction particle size distribution meter (SALD-3000J, produced by Shimadzu Corporation) according to a wet process was 2.5 μm.

Example 4

S-Tolvaptan Crystal Particle Formulation

An S-tolvaptan crystal (2.0 g, produced by Otsuka Pharmaceutical Co., Ltd.) was suspended in the medium solution of Example 1 (Table 1) (8.3 g) (equal to 10 mL). Zirconia beads (10 g) having a diameter of 1.5 mm were added to the suspension. A stirring bar was introduced into a container, and stirring was performed using a stirrer to perform bead pulverization (wet pulverization), thereby preparing 200 mg/mL of a homogeneous. S-tolvaptan crystal aqueous suspension. The mean particle size of the S-tolvaptan crystal particle measured during ultrasonic irradiation using a laser diffraction particle size distribution meter (SALD-3000J, produced by Shimadzu Corporation) according to a wet process was 2.5 μm.

Comparative Example 1

Preparation of Racemic Tolvaptan Spray-Dried (SD) Powder

A tolvaptan (racemic compound) crystal (20 g, produced by Otsuka Pharmaceutical Co., Ltd.) was dissolved in dichloromethane (150 mL) and ethanol (30 mL). Using a spray dryer (Pulvis GB22, produced by Yamato Scientific Co., Ltd.), the solution was spray-dried at a spraying air pressure of 0.1 MPa, a drying temperature of 80° C., an air flow of 0.45 m$^3$/min, and a liquid sending speed of 40 mL/min. The prepared spray-dried powder was dried under reduced pressure. In the powder X-ray diffraction of the prepared powder, only a halo peak was observed. Thus, the prepared powder was confirmed to be amorphous.

The mean particle size of the racemic tolvaptan SD powder measured using a laser diffraction particle size distribution meter (SALD-3000J, produced by Shimadzu Corporation) according to a wet process was 5.1 μm.

Comparative Example 2

Preparation of Racemic Tolvaptan SD Powder Containing 33% PLGA

A tolvaptan (racemic compound) crystal (10 g, produced by Otsuka Pharmaceutical Co., Ltd.) and a copolymer (5 g) of DL lactic acid and glycolic acid (PLGA-5005 produced by Wako Pure Chemical Industries) were dissolved in dichloromethane (100 mL) and ethanol (20 mL). Using a spray dryer (Pulvis GB22, produced by Yamato Scientific Co., Ltd.), the solution was spray-dried at a spraying air pressure of 0.1 MPa, a drying temperature of 80° C., an air flow of 0.44 m$^3$/min, and a liquid sending speed of 40 mL/min. The prepared spray-dried powder was dried under reduced pressure. In the powder X-ray diffraction of the prepared powder, only a halo peak was observed. Thus, the prepared powder was confirmed to be amorphous.

The mean particle size of the racemic tolvaptan SD powder containing 33% PLGA measured using a laser diffraction particle size distribution meter (SALD-3000J, produced by Shimadzu Corporation) according to a wet process was 5.1 μm.

Comparative Example 3

Preparation of Racemic Tolvaptan SD Powder Containing 33% PVP-17PF

A tolvaptan (racemic compound) crystal (10 g, produced by Otsuka Pharmaceutical Co., Ltd.) and polyvinylpyrrolidone (5 g, PVP-17PF, produced by BASF Ltd.) were dissolved in dichloromethane (100 mL) and ethanol (20 mL). Using a spray dryer (Pulvis GB22, produced by Yamato Scientific Co., Ltd.), the solution was spray-dried at a spraying air pressure of 0.1 MPa, a drying temperature of 80° C., an air flow of 0.41 m$^3$/min, and a liquid sending speed of 7 mL/min. The prepared spray-dried powder was dried under reduced pressure. In the powder X-ray diffraction of the prepared powder, only a halo peak was observed. Thus, the prepared powder was confirmed to be amorphous.

The mean particle size of the racemic tolvaptan SD powder containing 33% PVP-17PF measured using a laser diffraction particle size distribution meter (SALD-3000J, produced by Shimadzu Corporation) according to a wet process was 7.2 μm.

Comparative Example 4

Preparation of Racemic Tolvaptan SD Powder Containing 33% HP-55

A tolvaptan (racemic compound) crystal (10 g, produced by Otsuka Pharmaceutical Co., Ltd.) and hydroxypropyl methylcellulose phthalate (5 g) (HP-55 produced by Shin-Etsu Chemical Co., Ltd.) were dissolved in dichloromethane (150 mL) and ethanol (30 mL). Using a spray dryer (Pulvis GB22, produced by Yamato Scientific Co., Ltd.), the solution was spray-dried at a spraying air pressure of 0.1 MPa, at a drying temperature of 80° C., an air flow of 0.41 m$^3$/min, and a liquid sending speed of 40 mL/min. The prepared spray-dried powder was dried under reduced pressure. In the powder X-ray diffraction of the prepared powder, only a halo peak was observed. Thus, the prepared powder was confirmed to be amorphous.

The mean particle size of the racemic tolvaptan SD powder containing 33% HP-55 measured using a laser diffraction particle size distribution meter (SALD-3000J, produced by Shimadzu Corporation) according to a wet process was 5.5 μm.

Comparative Example 5

Preparation of Racemic Tolvaptan SD Powder Containing 33% HPC-SL

A tolvaptan (racemic compound) crystal (10 g, produced by Otsuka Pharmaceutical Co., Ltd.) and hydroxypropyl cellulose (5 g) (HPC-SL produced by Nippon Soda Co., Ltd.) were dissolved in dichloromethane (100 mL) and ethanol (30 mL). Using a spray dryer (Pulvis GB22, produced by Yamato Scientific Co., Ltd.), the solution was spray-dried at a spraying air pressure of 0.1 MPa, a drying temperature of 80° C., an air flow of 0.39 m$^3$/min, and a liquid sending speed of 7 mL/min. The prepared spray-dried powder was dried under reduced pressure. In the powder X-ray diffraction of the prepared powder, only a halo peak was observed. Thus, the prepared powder was confirmed to be amorphous.

A racemic tolvaptan SD powder containing 33% HPC-SL (300 mg) was loaded into a syringe, and the medium solution (0.76 g) of Example 1 (Table 1) was loaded into the other syringe. The two syringes were connected via a connector. Pumping was performed repeatedly to prepare 200 mg/mL of a homogeneous amorphous racemic tolvaptan aqueous suspension.

The mean particle size of the racemic tolvaptan SD powder containing 33% HPC-SL measured using a laser diffraction particle size distribution meter (SALD-3000J, produced by Shimadzu Corporation) according to a wet process was 6.6 μm.

Comparative Example 6

Preparation of Racemic Tolvaptan SD Powder

A tolvaptan (racemic compound) crystal (10 g, produced by Otsuka Pharmaceutical Co., Ltd.) was dissolved in dichloromethane (100 mL) and ethanol (20 mL). Using a spray dryer (an ODT-8 spray dryer, produced by Ohkawara Kakohki Co., Ltd.), the solution was spray-dried (rotary disk atomizer, a rotation speed of 13000 rpm, purge air pressure of 0/1 kg/cm$^2$, temperature at the hot air inlet of 90° C., liquid sending speed of 180 g/min). The prepared spray-dried powder was dried under reduced pressure. In the powder X-ray diffraction of the prepared powder, only a halo peak was observed. Thus, the prepared powder was confirmed to be amorphous.

The mean particle size of the racemic tolvaptan SD powder measured using a laser diffraction particle size distribution meter (SALD-3000J, produced by Shimadzu Corporation) according to a wet process was 32.5 µm.

Comparative Example 7

Preparation of Jet-Milled Powder of Racemic Tolvaptan Crystal

A tolvaptan (racemic compound) crystal (produced by Otsuka Pharmaceutical Co., Ltd.) was pulverized using a jet mill (PJM-100SP, produced by Nippon Pneumatic Mfg. Co., Ltd.) at an air pressure of 5 kgf/cm$^2$, and a sending speed of 20 rpm. The powder X-ray diffraction of the prepared powder was performed, and it was confirmed that the tolvaptan crystal was maintained.

The mean particle size of the racemic tolvaptan SD powder measured using a laser diffraction particle size distribution meter (SALD-3000J, produced by Shimadzu Corporation) according to a wet process was 2.4 µm.

Comparative Example 8

Preparation of Racemic Tolvaptan Crystal Particle

A tolvaptan (racemic compound) crystal (2.0 g) was suspended in the medium solution (8.3 g) of Example 1 (Table 1) (equal to 10 mL). Zirconia beads (10 g) having a diameter of 1.5 mm were added to the suspension. A stirring bar was introduced into a container, and stirring was performed using a stirrer to perform bead pulverization (wet pulverization), thereby preparing 200 mg/mL of a homogeneous racemic tolvaptan crystal aqueous suspension.

The mean particle size of the racemic tolvaptan crystal particle measured during ultrasonic irradiation using a laser diffraction particle size distribution meter (SALD-3000J, produced by Shimadzu Corporation) according to a wet process was 2.4 µm.

Test Example 1

Using human and rat liver homogenates (S9 fractions), the in vitro metabolic stability test of tolvaptan (racemic compound), R-tolvaptan, and S-tolvaptan was performed. The concentration of each evaluated compound was set to 100 nM, and the concentration sampling of each compound in a reaction mixture was conducted over time, i.e., 5, 10, 30, and 60 minutes after addition, and measured by LC-MS/MS (FIGS. 1 (1) and (2)).

The results indicated that in a human the S-tolvaptan disappeared slowly compared to tolvaptan (racemic compound) or R-tolvaptan, and had high metabolic stability (FIG. 1 (1)); and that in a rat the R-tolvaptan disappeared slowly compared to tolvaptan (racemic compound) or S-tolvaptan, and had high metabolic stability (FIG. 1 (2)).

Test Example 2

Figure 2:
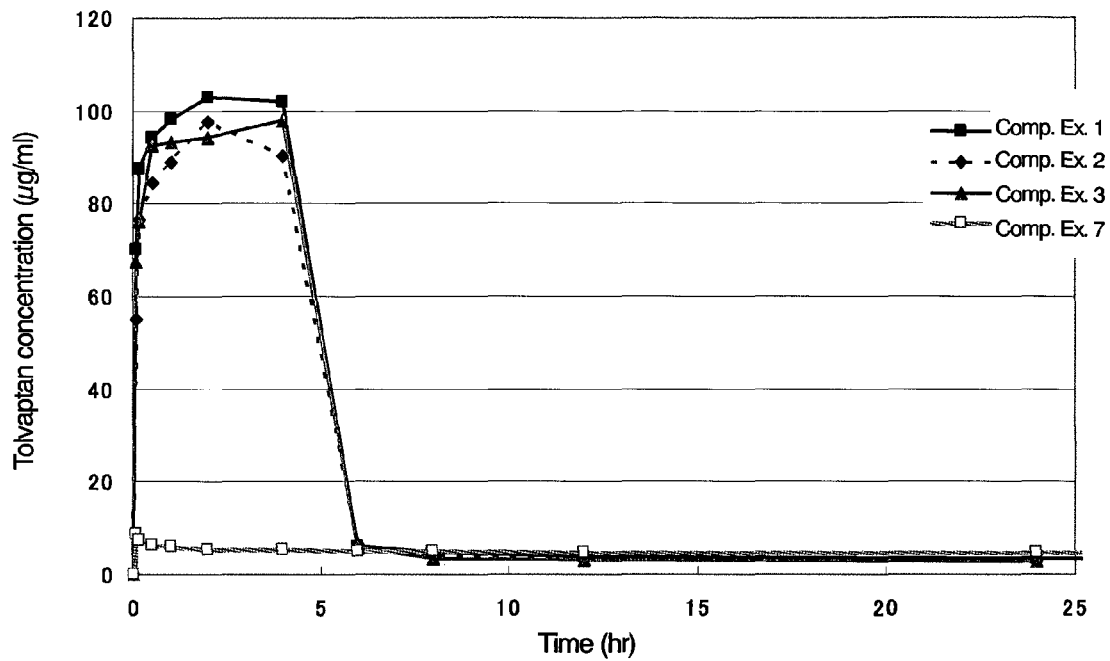
FIG. 2 shows the results of a dissolution test for the spray-dried powders of Comparative Examples 1 to 3, which contain amorphous racemic tolvaptan; and the jet-milled powder of crystalline racemic tolvaptan of Comparative Example 7 in Test Example 2.
Figure 3:
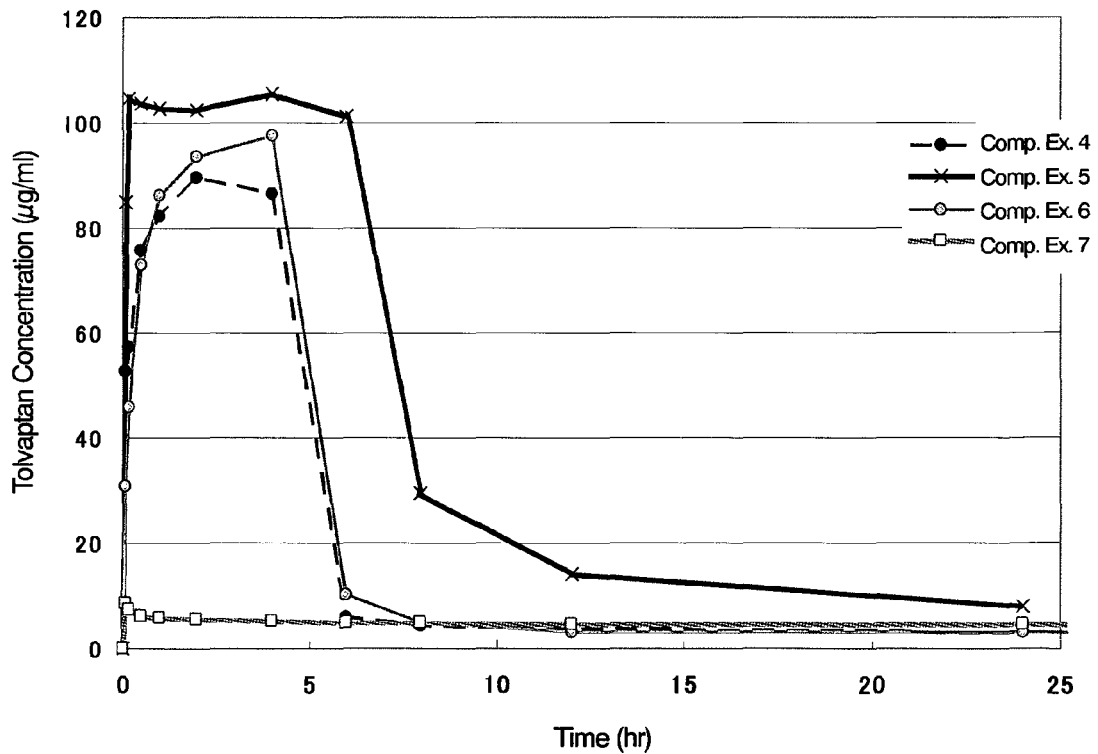
FIG. 3 shows the results of a dissolution test for the spray-dried powders of Comparative Examples 4 to 6, which contain amorphous racemic tolvaptan; and the jet-milled powder of crystalline racemic tolvaptan of Comparative Example 7 in Test Example 2.
Figure 4:
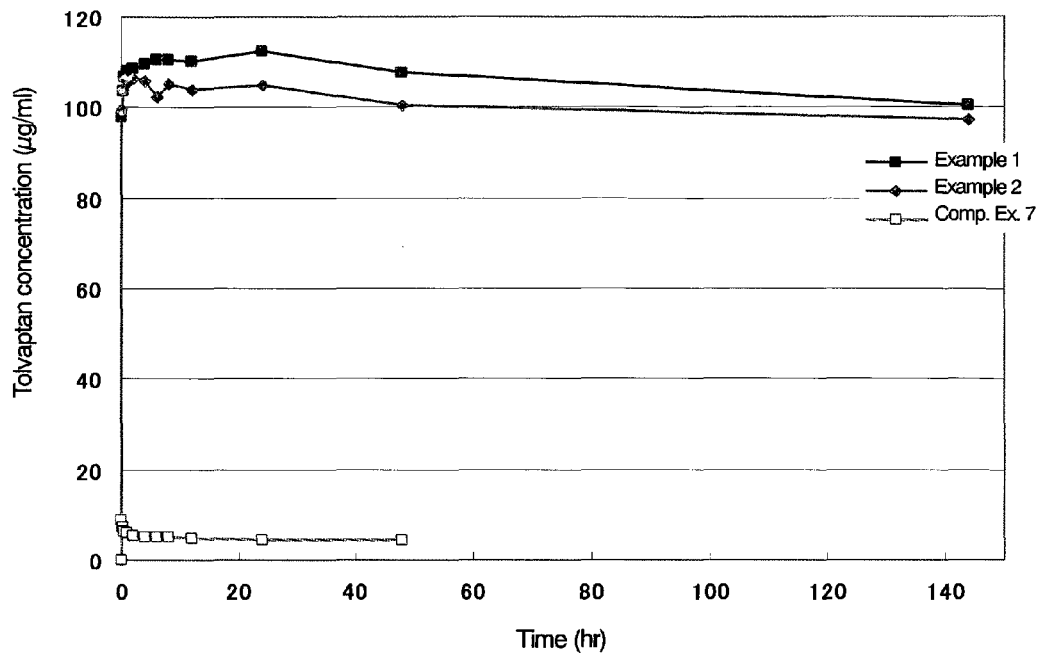
FIG. 4 shows the results of a dissolution test for the spray-dried powders of Examples 1 and 2, which contain amorphous optically active tolvaptan (R-form or S-form); and the jet-milled powder of crystalline racemic tolvaptan of Comparative Example 7 in Test Example 2.

The dissolution test of each of the R- and S-tolvaptan SD powders of Examples 1 and 2, tolvaptan (racemic compound) SD powders of Comparative Examples 1 to 6, and tolvaptan (racemic compound) crystal powder of Comparative Example 7 was performed (FIGS. 2 to 4). In the dissolution test method, the R- and S-tolvaptan SD powders, tolvaptan (racemic compound) SD powders, and tolvaptan (racemic compound) crystal powder were weighed out in individual amounts of 0.1 g, and added to a solution (500 mL) for dissolution test shown in Table 2. None of the tolvaptans in an amount weighed above were dissolved in the solvent for dissolution test, and were fully suspended. Sequential sampling was performed 0.083, 0.167, 0.5, 1, 2, 4, 6, 8, 12, 24, 48, and 144 hours after addition.

TABLE 2

| Composition of the solution for dissolution test | |
|---|---|
| | Quantity (mg/mL) |
| Polysorbate 80 | 1.0 |
| Sodium dihydrogen phosphate | 2.15 |
| Sodium hydroxide | q.s. to pH 7.4 |
| Purified water | q.s. |

The results indicated that the dissolution amount of the tolvaptan (racemic compound) crystal of Comparative Example 7 was remarkably low from the beginning. The amorphous tolvaptans (racemic compounds) of Comparative Examples 1 to 6 showed high concentrations for several hours after the beginning of the dissolution test. Thereafter, the dissolution amounts were suddenly reduced in 10 hours, and then reduced to the level that was the same as the dissolution amount of the tolvaptan (racemic compound) crystal. The R-tolvaptan SD powder and the S-tolvaptan SD powder of Examples 1 and 2 did not show a remarkable reduction in dissolution amount within at least 144 hours after the beginning of the dissolution test.

Test Example 3

The dissolution test of each of the R- and S-tolvaptan crystal powders was performed (FIG. 5). As a control, the result of Comparative Example 7 in Test Example 2 above was plotted. In the dissolution test method, an R-tolvaptan crystal powder (mean particle size: 34.0 µm) or an S-tolvaptan crystal powder (mean particle size: 35.8 µm) was weighed out in an amount of 0.1 g, and added to the solution for the dissolution test (500 mL) shown in Table 2 above. None of the tolvaptans in an amount weighed above were dissolved in the solution for dissolution test, and were fully suspended. Sequential sampling was performed 0.083, 0.167, 0.5, 1, 2, 4, 6, 8, 12, 24, and 48 hours after addition.

The results indicated that although the dissolution amount of the tolvaptan (racemic compound) crystal of Comparative Example 7 was slightly high immediately after the beginning of the test, the dissolution rate was decreased immediately thereafter. Two hours later, the dissolution amounts of the R-tolvaptan crystal and the S-tolvaptan crystal were slightly higher than that of the tolvaptan (racemic compound) crystal of Comparative Example 7, and remained fairly constant. A reduction in dissolution amount as in Comparative Example 7 was not observed within at least 48 hours after the beginning of the dissolution test.

Test Example 4

The optically active tolvaptan aqueous suspensions of Examples 1, 2, 3, and 4 and the racemic tolvaptan aqueous suspensions of Comparative Examples 5 and 8 were each intramuscularly administered at a dose of 100 mg/kg to the thigh muscle of individual SD female rats under light anesthesia with diethylether using a syringe equipped with a 24G needle (n=4). Approximately 0.5 mL of blood was collected from the jugular vein under light anesthesia with diethylether 1 hour, 6 hours, 1 day, days, 7 days, 14 days, 21 days, and 28 days after the administration of each formulation (aqueous suspension). The collected bloods were each introduced into individual Separapid tubes, left at room temperature for about 30 minutes, and then centrifuged at 1800×g for 10 minutes to obtain serums. The obtained serums were preserved at −20° C. or less until measurement. The tolvaptan concentration of each serum was measured by an LC-MS/MS method (n=4).

(1) Comparison Between Crystalline Optically Active Tolvaptan and Crystalline Racemic Tolvaptan The R-tolvaptan crystal aqueous suspension of Example 3, the S-tolvaptan crystal aqueous suspension of Example 4, and the tolvaptan (racemic compound) crystal aqueous suspension of Comparative Example 8 were each administered to individual female SD rats.

The thigh, which was the administration site, was open 28 days after administration to confirm remaining tolvaptan. The tolvaptan was extracted from each cyst. The tolvaptan in the cyst was extracted with acetonitrile, diluted with acetonitrile and methanol, and filtered using a filter (pore diameter: 0.2 μm). The remaining rate of the tolvaptan was then measured by HPLC (n=3).

The results indicate that the remaining rate of the tolvaptan (racemic compound) crystal of Comparative Example 8 was about 70%; that the absorption rate was too slow as a formulation administered every four weeks; that the remaining rate of each of Example 3 (R-tolvaptan crystal) and Example 4 (S-tolvaptan crystal) was about 50%; and that in all of the Examples, tolvaptan in an amount suitable for a formulation administered every four weeks was absorbed in four weeks (Table 3).

TABLE 3

Remaining rate of formulations at administration site

| | Mean remaining rate (%) (mean ± SD, n = 3) |
|---|---|
| Example 3 (R-tolvaptan crystal) | 48.6 ± 8.3 |
| Example 4 (S-tolvaptan crystal) | 49.0 ± 0.9 |
| Comparative Example 8 (tolvaptan (racemic) crystal) | 68.3 ± 8.3 |

Further, FIG. 6 indicates the results of serum tolvaptan concentration profile for 28 days after the intramuscular administration of the R-tolvaptan crystal aqueous suspension of Example 3 and the tolvaptan (racemic compound) crystal aqueous suspension of Comparative Example 8 (n=4). The R-tolvaptan crystal of Example 3 showed a significantly high serum concentration profile for 4 weeks after administration compared to the tolvaptan (racemic compound) crystal of Comparative Example 8.

(2) Comparison Between Amorphous Optically Active Tolvaptan and Amorphous Racemic Tolvaptan The amorphous R-tolvaptan aqueous suspension of Example 1, amorphous S-tolvaptan aqueous suspension of Example 2, and amorphous tolvaptan (racemic compound) aqueous suspension of Comparative Example 5 were each administered to individual female SD rats. In the same manner as Item (1) above, the remaining rate of tolvaptan at the administration site 28 days after administration was measured (n=3).

The results indicated that the remaining rate of the amorphous tolvaptan (racemic compound) of Comparative Example 5 was about 20%, that no amorphous S-tolvaptan of Example 2 remained, and that the remaining rate of the amorphous R-tolvaptan of Example 1 was about 4%. It was found that the absorption rates of the amorphous R-tolvaptan of Example 1 and the amorphous S-tolvaptan of Example 2 were faster than that of the amorphous tolvaptan (racemic compound) (Table 4).

TABLE 4

| | Mean remaining rate (%) (mean ± SD, n = 3) |
|---|---|
| Example 1 (Amorphous R-tolvaptan) | 4.2 ± 4.5 |
| Example 2 (Amorphous S-tolvaptan) | N.D.* |
| Comparative Example 5 (Amorphous racemic tolvaptan) | 21.1 ± 8.0 |

*Not detected in all cases

Further, FIG. 7 indicates the results of serum tolvaptan concentration profile for 28 days after intramuscular administration (n=4). The amorphous R-tolvaptan of Example 1 showed a significantly high serum concentration profile for 4 weeks after administration compared to the amorphous tolvaptan (racemic compound) of Comparative Example 5.

Figure 8:
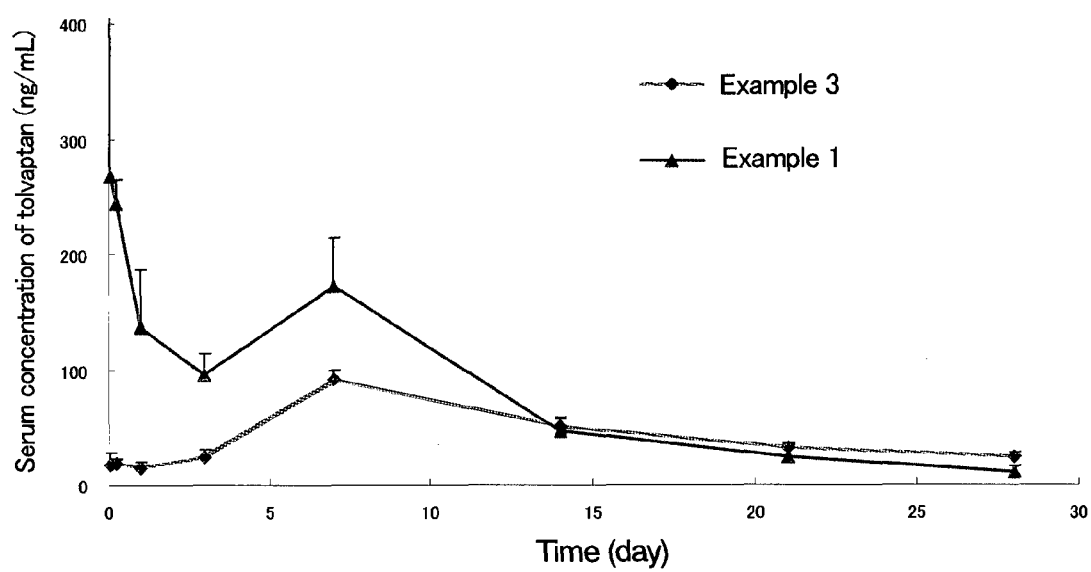
FIG. 8 shows profiles of serum concentration of tolvaptan when an aqueous suspension containing a crystalline R-tolvaptan particle (Example 3) and an aqueous suspension containing an amorphous R-tolvaptan powder (Example 1) are each individually administered intramuscularly in an amount of 100 mg/kg to female rats in (3) of Test Example 4.

(3) Comparison Between Crystalline Optically Active Tolvaptan and Amorphous Optically Active Tolvaptan The R-tolvaptan crystal aqueous suspension of Example 3 and the amorphous R-tolvaptan aqueous suspension of Example 1 were each administered to individual female SD rats. FIG. 8 indicates the results of serum concentration profile for 28 days after intramuscular administration. In contrast to the amorphous R-tolvaptan of Example 1, the R-tolvaptan crystal of Example 3 did not show a high serum concentration immediately after administration (initial burst, etc.), and the serum concentration of a therapeutically effective amount can be maintained for 4 weeks after administration. In particular, the serum concentration of the R-tolvaptan crystal of Example 3 did not change greatly. The serum concentration of the R-tolvaptan crystal of Example 3 from day 14 was higher than that of the amorphous R-tolvaptan of Example 1 from day 14. Therefore, the R-tolvaptan crystal of Example 3 was found to be suitable as a depot injection administered every 4 weeks.

As shown in Tables 3 and 4 above, the remaining rate of the R-tolvaptan crystal of Example 3 was about 50%, and the remaining rate of the amorphous R-tolvaptan of Example 1 was about 4%.

Example 5

S-Tolvaptan Crystal Particle Aqueous Suspension

An S-tolvaptan crystal (15.0 g, produced by Otsuka Pharmaceutical Co., Ltd.) was suspended in the medium solution (38.0 g) shown in Table 5 (equal to 50 mL of the formulation). Zirconia beads (50 g) having a diameter of 1.5 mm were added to the suspension. The content of the container was stirred to perform bead pulverization (wet pulverization), thereby preparing an S-tolvaptan crystal particle aqueous suspension.

The mean particle size of the S-tolvaptan crystal particle measured during ultrasonic irradiation using a laser diffraction particle size distribution meter (SALD-3000J, produced by Shimadzu Corporation) according to a wet process was 3.0 µm.

TABLE 5

Composition of medium solution (per mL of formulation)

| | Prescribed amount |
|---|---|
| Sodium carboxymethyl cellulose | 6.0 mg |
| Povidone K17 | 3.0 mg |
| D-mannitol | 35.0 mg |
| Sodium dihydrogen phosphate monohydrate | 0.9 mg |
| Sodium hydroxide | q.s. to pH 7.0 |
| Water for injection | q.s. to 1 mL |
| Total weight | 0.76 g |

Example 6

R-Tolvaptan Crystal Particle Aqueous Suspension

An R-tolvaptan crystal (30.0 g, produced by Otsuka Pharmaceutical Co., Ltd.) was suspended in the medium solution (76.0 g) of Example 5 (Table 5) (equal to 100 mL of the formulation). Zirconia beads (150 g) having a diameter of 1.5 mm were added to the suspension. The content of the container was stirred to perform bead pulverization (wet pulverization), thereby preparing an R-tolvaptan crystal particle aqueous suspension.

The mean particle size of the R-tolvaptan crystal particle measured during ultrasonic irradiation using a laser diffraction particle size distribution meter (SALD-3000J, produced by Shimadzu Corporation) according to a wet process was 1.9 µm.

Table 6 shows the composition of each of the formulations prepared in Examples 5 and 6.

TABLE 6

Composition of formulations (per mL of formulation)

| | Example 5 S-tolvaptan crystal particle aqueous suspension | Example 6 R-tolvaptan crystal particle aqueous suspension |
|---|---|---|
| Tolvaptan | 300 mg | 300 mg |
| Sodium carboxymethyl cellulose | 6.0 mg | 6.0 mg |
| Povidone K17 | 3.0 mg | 3.0 mg |
| D-mannitol | 35.0 mg | 35.0 mg |
| Sodium dihydrogen phosphate monohydrate | 0.9 mg | 0.9 mg |
| Sodium hydroxide | q.s. to pH 7.0 | q.s. to pH 7.0 |
| Total weight | 1.06 g | 1.06 g |

Test Example 5

The effects of the S-tolvaptan crystal particle aqueous suspension obtained in Example 5 against polycystic kidney disease were evaluated using pcy mice (male), which are polycystic kidney disease model animals.

Based on the body weight and the kidney volume measured by MRI at 4 weeks of age, the pcy mice were divided into two groups: (1) a control group; and (2) a group receiving the S-tolvaptan crystal particle aqueous suspension. As normal control mice, DBA/2JJcl mice were used.

An S-tolvaptan crystal particle aqueous suspension that was diluted to 200 mg/mL was subcutaneously injected to the group receiving the S-tolvaptan crystal particle aqueous suspension in an amount of 1000 mg/kg at 6 and 10 weeks of age. The drug treatment was started from 6 weeks of age, and autopsy was conducted at 16 weeks of age. During autopsy, the right and left kidneys were collected, and the weight of the kidneys was adjusted based on the body weight and evaluated.

Table 7 shows the results of kidney weight evaluated at 16 weeks of age (10 weeks after the beginning of the experiment). Compared to normal DBA mice, an increase in kidney weight was observed in pcy control mice at 16 weeks of age. An increase in kidney weight was significantly suppressed in the group receiving the S-tolvaptan crystal particle aqueous suspension, compared to the pcy control group.

Figure 9:
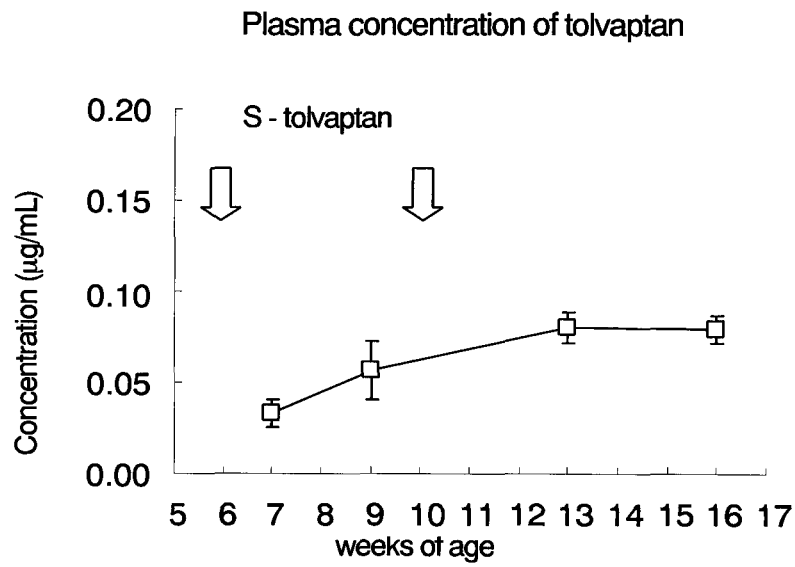
FIG. 9 shows a profile of plasma concentration of tolvaptan when a crystalline S-tolvaptan particle aqueous suspension (Example 5) is administered subcutaneously in an amount of 1000 mg/kg to pcy mice (male) in Test Example 5.

FIG. 9 shows the plasma tolvaptan concentration measured at 7, 9, 13, and 16 weeks of age. By the administration of the S-tolvaptan crystal particle aqueous suspension at 6 and 10 weeks of age, the plasma tolvaptan concentrations of the pcy mice were maintained in a stable manner until the end of the experiment (16 weeks of age).

TABLE 7

Kidney weight of (16-week-old) pcy mice (% BW)

| | Group of mice | Number of mice | Kidney weight (% BW) Mean ± SE | Assay results Comparison with the control group |
|---|---|---|---|---|
| 1 | Normal DBA | 5 | 1.52 ± 0.05 | — |
| 2 | pcy control | 10 | 8.09 ± 0.60 | — |
| 3 | pcy receiving the S-tolvaptan crystal particle aqueous suspension (1000 mg/kg SC) | 9 | 5.46 ± 0.37 | p < 0.01 |

Each value indicates the mean value ± SEM.
For comparison with the control group, two-tailed t-test was used.

Test Example 6

The effects of the R-tolvaptan crystal particle aqueous suspension obtained in Example 6 against polycystic kidney disease were evaluated using PCK rats (male), which are polycystic kidney disease model animals.

Based on the plasma albumin level and the kidney volume measured by MRI at 12 weeks of age, the PCK rats were divided into two groups: (1) a control group; and (2) a group receiving the R-tolvaptan crystal particle aqueous suspension. As normal control rats, Crl:CD(SD) rats were used.

The R-tolvaptan crystal particle aqueous suspension (300 mg/mL) was intramuscularly injected to the right and left gastrocnemius muscle of the group receiving the R-tolvaptan crystal particle aqueous suspension in an amount of 400 mg/kg at 14, 15, and 20 weeks of age. The drug treatment was started from 14 weeks of age. At 24 weeks of age, the right kidney volume was measured again by MRI, and as an index of cystic kidney, a change in the kidney volume between before and after drug administration was evaluated.

Table 8 shows change in the right kidney volume (Δ mm$^3$) calculated from the right kidney volume measured by MRI at 12 weeks of age (at the time of grouping) and 24 weeks of age. The right kidney volume of the PCK control rats at 12 weeks of age was 3595±162 mm³, and it was increased about 1.4-fold due to cystic enlargement until the 24 weeks of age. An increase in kidney volume was significantly suppressed in the group receiving the R-tolvaptan crystal particle aqueous suspension (P<0.05).

Figure 10:
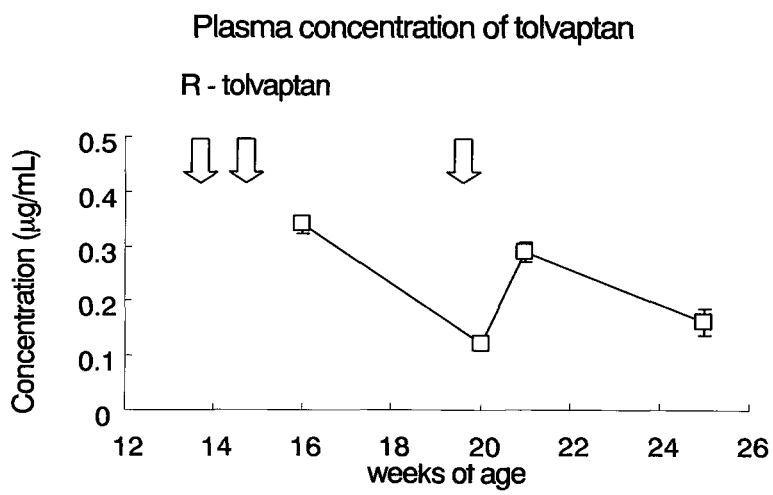
FIG. 10 shows a profile of plasma concentration of tolvaptan when a crystalline R-tolvaptan particle aqueous suspension (Example 6) is administered intramuscularly in an amount of 400 mg/kg to PCK rats (male) in Test Example 6.

FIG. 10 shows the plasma tolvaptan concentration measured at 16, 20, 21, and 25 weeks of age. By the administration of R-tolvaptan crystal particle aqueous suspension at 14, 15, and 20 weeks of age, the plasma tolvaptan concentrations of the PCK rats were maintained in a stable manner until the end of the experiment (25 weeks of age).

TABLE 8

Change in right kidney volume of PCK rats (change between 12-week-old and 24-week-old)

| | Group of rats | Number of rats | Change in right kidney volume (Δ mm³) Mean ± SE | Assay results Comparison with the control group |
|---|---|---|---|---|
| 1 | Normal SD | 5 | 404 ± 34 | — |
| 2 | PCK control | 10 | 1337 ± 157 | — |
| 3 | PCK receiving the R-tolvaptan crystal particle aqueous suspension (400 mg/kg IM) | 9 | 818 ± 73 | p < 0.05 |

Each value indicates the mean value ± SEM.
For comparison with the control group, two-tailed t-test was used.

The above results show that since the aqueous suspension containing crystalline optically active tolvaptan can sustainably maintain the plasma tolvaptan concentration in pcy mice and PCK rats, which are polycystic kidney disease model animals, the development of polycystic kidney disease can be suppressed.

The invention claimed is:

1. An injectable depot formulation comprising:
    (1) particles containing a therapeutically effective amount of optically active tolvaptan as an active ingredient; and
    (2) a pharmaceutically acceptable carrier for injection,
    wherein the particles (1) have a mean particle size of about 0.2 to 100 μm.

2. The injectable depot formulation according to claim 1, wherein the optically active tolvaptan in the particles (1) is tolvaptan consisting essentially of R-tolvaptan or tolvaptan consisting essentially of S-tolvaptan.

3. The injectable depot formulation according to claim 1 or 2, wherein the content of the optically active tolvaptan in the particles (1) is 50 to 100% by weight.

4. The injectable depot formulation according to claim 3, wherein the particles (1) consist essentially of the optically active tolvaptan.

5. The injectable depot formulation according to claim 1 or 2, wherein the pharmaceutically acceptable carrier for injection (2) comprises
    (a) a suspending agent and/or a wetting agent
    (b) optionally, a tonicity agent and/or a bulking agent,
    (c) optionally, a buffer,
    (d) optionally, a pH-adjusting agent,
    (e) optionally, a viscosity-enhancing agent, and
    (f) optionally, a preservative.

6. The injectable depot formulation according to claim 5, wherein the suspending agent is sodium carboxymethyl cellulose and polyvinylpyrrolidone.

7. The injectable depot formulation according to claim 5, wherein the wetting agent is polysorbate 80 and/or a poloxamer.

8. The injectable depot formulation according to claim 1 or 2, wherein the particles (1) contain a water-soluble polymer and/or a biodegradable polymer.

9. The injectable depot formulation according to claim 8, wherein the water-soluble polymer is at least one member selected from the group of hydroxypropyl cellulose, polyvinylpyrrolidone, and hydroxypropyl methylcellulose phthalate, and the biodegradable polymer is at least one member selected from the group of polylactic acids and polylactic acid-polyglycolic acid copolymers.

10. The injectable depot formulation according to claim 1 or 2, wherein the optically active tolvaptan is amorphous.

11. The injectable depot formulation according claim 1 or 2, wherein the optically active tolvaptan is crystalline.

12. The injectable depot formulation according to claim 1 or 2, which further comprises (3) water for injection and is in the form of an aqueous suspension.

13. The injectable depot formulation according to claim 12, wherein the concentration of the optically active tolvaptan contained in the particles (1) in the aqueous suspension is 100 mg/ml to 500 mg/ml.

14. A process for producing an injectable depot formulation, the process comprising mixing (1) particles containing a therapeutically effective amount of optically active tolvaptan as an active ingredient and (2) a pharmaceutically acceptable carrier for injection,
    wherein the particles (1) have a mean particle size of about 0.2 to 100μm.

* * * * *